(12) United States Patent
Nara et al.

(10) Patent No.: US 8,071,300 B2
(45) Date of Patent: Dec. 6, 2011

(54) DRUG-PHOSPHORYLATING ENZYME

(75) Inventors: Futoshi Nara, Chiba (JP); Kiyoaki Yonesu, Tokyo (JP); Kazuishi Kubota, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 277 days.

(21) Appl. No.: 12/376,434

(22) PCT Filed: Aug. 3, 2007

(86) PCT No.: PCT/JP2007/065232
§ 371 (c)(1),
(2), (4) Date: Mar. 10, 2009

(87) PCT Pub. No.: WO2008/016133
PCT Pub. Date: Feb. 7, 2008

(65) Prior Publication Data
US 2010/0248227 A1   Sep. 30, 2010

(30) Foreign Application Priority Data

Aug. 4, 2006   (JP) .................................. 2006-213734

(51) Int. Cl.
*C12Q 1/68* (2006.01)
*C12P 7/62* (2006.01)
*G01N 33/53* (2006.01)

(52) U.S. Cl. ............................ 435/6.1; 435/7.4; 435/135

(58) Field of Classification Search .......................... None
See application file for complete search history.

(56) References Cited

FOREIGN PATENT DOCUMENTS

| | | |
|---|---|---|
| EP | 0627406 A1 | 7/1994 |
| EP | 0778263 A1 | 6/1997 |
| EP | 1002792 A1 | 5/2000 |
| EP | 1300405 A1 | 4/2003 |
| EP | 1431275 A1 | 6/2004 |
| EP | 1431284 A1 | 6/2004 |
| EP | 1471054 A1 | 10/2004 |
| JP | 2005-46141 A | 2/2005 |
| JP | 2005-47899 A | 2/2005 |
| JP | 2005-206586 A | 8/2005 |
| WO | 03/089601 A2 | 10/2003 |
| WO | 03/093311 A1 | 11/2003 |
| WO | 2005/005383 A1 | 1/2005 |
| WO | 2005/063671 A1 | 7/2005 |
| WO | 2005/079463 A2 | 9/2005 |
| WO | 2006/138609 A2 | 12/2006 |

OTHER PUBLICATIONS

Szwergold et al, Human fructosamine-3-kinase: purification, sequencing, substrate specificity, and evidence of activity in vivo. Diabetes. Sep. 2001;50(9):2139-47.*

Perlin et al, Developing a snapshot of the ATP binding domain(s) of aminoglycoside phosphotransferases. Front Biosci. Jan. 1, 1999;4:D63-71.*

Delpierre et al, Identification, cloning, and heterologous expression of a mammalian fructosamine-3-kinase. Diabetes 49 (10), 1627-1634 (2000).*

Billich, A., et al., "Phosphorylation of the Immunomodulatory Drug FTY720 by Sphingosine Kinases," Journal of Biological Chemistry 278(48):47408-47415, Nov. 2003.

Collard, F., et al., "Fructosamine 3-Kinase-Related Protein and Deglycation in Human Erythrocytes," Biochemical Journal 382(Pt. 1):137-143, Aug. 2004.

Collard, F., et al., "A Mammalian Protein Homologous to Fructosamine-3-Kinase Is a Ketosamine-3-Kinase Acting on Psicosamines and Ribulosamines but Not on Fructosamines," Diabetes 52(12):2888-2895, Dec. 2003.

Conner, J.R., et al., "The Expression of the Genes for Fructosamine-3-Kinase and Fructosamine-3-Kinase-Related Protein Appears to Be Constitutive and Unaffected by Environmental Signals," Biochemical and Biophysical Research Communications 323(3):932-936, Oct. 2004.

Conner, J.R., et al., "Some Clues as to the Regulation, Expression, Function, and Distribution of Fructosamine-3-Kinase and Fructosamine-3-Kinase-Related Protein," Annals of the New York Academy of Sciences 1043:824-836, Jun. 2005.

Delpierre, G., et al., "Identification, Cloning, and Heterologous Expression of a Mammalian Fructosamine-3-Kinase," Diabetes 49(10):1627-1634, Oct. 2000.

Delpierre, G., et al., "Variability in Erythrocyte Fructosamine 3-Kinase Activity in Humans Correlates With Polymorphisms in the FN3K Gene and Impacts on Haemoglobin Glycation at Specific Sites," Diabetes and Metabolism 32(1):31-39, Feb. 2006.

Delplanque, J., et al., "Tissue Distribution and Evolution of Fructosamine 3-Kinase and Fructosamine 3-Kinase-Related Protein," Journal of Biological Chemistry 279(45):46606-46613, Nov. 2004.

Hänel, P., et al., "Erythrocytes Store and Release Sphingosine 1-Phosphate in Blood," FASEB [Federation of American Societies for Experimental Biology] Journal 21(4):1202-1209, Apr. 2007.

Krause, R., et al., "A Convenient HPLC Assay for the Determination of Fructosamine-3-Kinase Activity in Erythrocytes," Analytical and Bioanalytical Chemistry 386(7-8):2019-2025, Dec. 2006.

Szwergold, B., et al., "Fructosamine-3-Kinase-Related Protein Phosphorylates Glucitolamines on the C-4 Hydroxyl: Novel Substrate Specificity of an Enigmatic Enzyme," Biochemical and Biophysical Research Communications 361(4):870-875, Oct. 2007.

Szwergold, B., et al., "Human Fructosamine-3-Kinase: Purification, Sequencing, Substrate Specificity, and Evidence of Activity In Vivo," Diabetes 50(9):2139-2147, Sep. 2001.

* cited by examiner

*Primary Examiner* — Tekchand Saidha
*Assistant Examiner* — M D. Younus Meah
(74) *Attorney, Agent, or Firm* — Christensen O'Connor Johnson Kindness PLLC

(57) ABSTRACT

The objects of the present invention are: elucidation of an enzyme that phosphorylates in vivo a compound such as (2R)-2-amino-2-methyl-4-[5-(5-phenylpentanoyl)thiophen-2-yl]butan-1-ol and provision of a method of phosphorylating the aforementioned compound; provision of a method of screening for a substance phosphorylated by the aforementioned enzyme; provision of a method of determining the ability of a subject to phosphorylate a test compound.

Provision of a method of phosphorylating the aforementioned compound using a human fructosamine-3-kinase-related protein and/or fructosamine-3-kinase, and a method of determining the ability of a subject to phosphorylate a test compound.

4 Claims, 4 Drawing Sheets

```
                         SEQUENCE LISTING

<160> NUMBER OF SEQ ID NOS: 8

<210> SEQ ID NO 1
<211> LENGTH: 1466
<212> TYPE: DNA
<213> ORGANISM: Homo sapiens
<220> FEATURE:
<221> NAME/KEY: CDS
<222> LOCATION: (6)..(935)

<400> SEQUENCE: 1 actcc atg gag cag ctg ctg cgc gcc gag ctg cgc acc gcg acc ctg cgg        50
      Met Glu Gln Leu Leu Arg Ala Glu Leu Arg Thr Ala Thr Leu Arg
      1               5                  10                  15 gcc ttc ggc ggc ccc ggc gcc ggc tgc atc agc gag ggc cga gcc tac          98
Ala Phe Gly Gly Pro Gly Ala Gly Cys Ile Ser Glu Gly Arg Ala Tyr
                 20                  25                  30 gac acg gac gca ggc cca gtg ttc gtc aaa gtc aac cgc agg acg cag         146
Asp Thr Asp Ala Gly Pro Val Phe Val Lys Val Asn Arg Arg Thr Gln
             35                  40                  45 gcc cgg cag atg ttt gag ggg gag gtg gcc agc ctg gag gcc ctc cgg         194
Ala Arg Gln Met Phe Glu Gly Glu Val Ala Ser Leu Glu Ala Leu Arg
         50                  55                  60 agc acg ggc ctg gtg cgg gtg ccg agg ccc atg aag gtc atc gac ctg         242
Ser Thr Gly Leu Val Arg Val Pro Arg Pro Met Lys Val Ile Asp Leu
     65                  70                  75 ccg gga ggt ggg gcc gcc ttt gtg atg gag cat ttg aag atg aag agc         290
Pro Gly Gly Gly Ala Ala Phe Val Met Glu His Leu Lys Met Lys Ser
 80                  85                  90                  95 ttg agc agt caa gca tca aaa ctt gga gag cag atg gca gat ttg cat         338
Leu Ser Ser Gln Ala Ser Lys Leu Gly Glu Gln Met Ala Asp Leu His
                100                 105                 110 ctt tac aac cag aag ctc agg gag aag ttg aag gag gag aac aca         386
Leu Tyr Asn Gln Lys Leu Arg Glu Lys Leu Lys Glu Glu Asn Thr
                115                 120                 125
```

```
gtg ggc cga aga ggt gag ggt gct gag cct cag tat gtg gac aag ttc     434
Val Gly Arg Arg Gly Glu Gly Ala Glu Pro Gln Tyr Val Asp Lys Phe
        130                 135                 140 ggc ttc cac acg gtg acg tgc tgc ggc ttc atc ccg cag gtg aat gag     482
Gly Phe His Thr Val Thr Cys Cys Gly Phe Ile Pro Gln Val Asn Glu
145                 150                 155 tgg cag gat gac tgg ccg acc ttt ttc gcc cgg cac cgg ctc cag gcg     530
Trp Gln Asp Asp Trp Pro Thr Phe Phe Ala Arg His Arg Leu Gln Ala
160                 165                 170                 175 cag ctg gac ctc att gag aag gac tat gct gac cga gag gca cga gaa     578
Gln Leu Asp Leu Ile Glu Lys Asp Tyr Ala Asp Arg Glu Ala Arg Glu
                180                 185                 190 ctc tgg tcc cgg cta cag gtg aag atc ccg gat ctg ttt tgt ggc cta     626
Leu Trp Ser Arg Leu Gln Val Lys Ile Pro Asp Leu Phe Cys Gly Leu
            195                 200                 205 gag att gtc ccc gcg ttg ctc cac ggg gat ctc tgg tcg gga aac gtg     674
Glu Ile Val Pro Ala Leu Leu His Gly Asp Leu Trp Ser Gly Asn Val
        210                 215                 220 gct gag gac gac gtg ggg ccc att att tac gac ccg gct tcc ttc tat     722
Ala Glu Asp Asp Val Gly Pro Ile Ile Tyr Asp Pro Ala Ser Phe Tyr
225                 230                 235 ggc cat tcc gag ttt gaa ctg gca atc gcc ttg atg ttt ggg ggg ttc     770
Gly His Ser Glu Phe Glu Leu Ala Ile Ala Leu Met Phe Gly Gly Phe
240                 245                 250                 255 ccc aga tcc ttc ttc acc gcc tac cac cgg aag atc ccc aag gct ccg     818
Pro Arg Ser Phe Phe Thr Ala Tyr His Arg Lys Ile Pro Lys Ala Pro
                260                 265                 270 ggc ttc gac cag cgg ctg ctc ctc tac cag ctg ttt aac tac ctg aac     866
Gly Phe Asp Gln Arg Leu Leu Leu Tyr Gln Leu Phe Asn Tyr Leu Asn
            275                 280                 285 cac tgg aac cac ttc ggg cgg gag tac agg agc cct tcg ttg ggc acc     914
His Trp Asn His Phe Gly Arg Glu Tyr Arg Ser Pro Ser Leu Gly Thr
        290                 295                 300 atg cga agg ctg ctc aag tag cggcccctgc cctcccttcc cctgtccccg        965
Met Arg Arg Leu Leu Lys
305 tccccgtctc cgtctccccg tcctgtccc cccgtccccc gtccctgtgc cccgtccct    1025 gtccccctgt tcccgtctcc cgtccctcc gtctccatcc cccgtcccc ccatcctcct    1085 gtccccgtcc cccgtcccc gtcctcat ccctgtccc cgtcccctg tcctgtccc       1145 cctgtccaca taccaatccc cctgtccccg accccatcc ccgtccccca tctccgtccc   1205 cgtccccct gccccgtccc cgtctccgtt cccccgtccc catcctccat cccgtctcc    1265 catcgccgtc cccccgtccc cgtccccgt ccccccgtgc cccgtcccc gtcccctg    1325 tccctgtccc ccttcccccg accctccca gatcctgggg accaataaag cccgcagcgg   1385 gcctcggctg gcgaaaaaaa aaaaaaaaaa aaaaaaaaaa aaaaaaaaaa aaaaaaaaaa   1445 aaaaaaaaaa aaaaaaaaaa a                                           1466

<210> SEQ ID NO 2
<211> LENGTH: 309
<212> TYPE: PRT
<213> ORGANISM: Homo sapiens

<400> SEQUENCE: 2

Met Glu Gln Leu Leu Arg Ala Glu Leu Arg Thr Ala Thr Leu Arg Ala
1               5                   10                  15

Phe Gly Gly Pro Gly Ala Gly Cys Ile Ser Glu Gly Arg Ala Tyr Asp
            20                  25                  30
```

```
Thr Asp Ala Gly Pro Val Phe Val Lys Val Asn Arg Arg Thr Gln Ala
    35                  40                  45

Arg Gln Met Phe Glu Gly Glu Val Ala Ser Leu Glu Ala Leu Arg Ser
50                  55                  60

Thr Gly Leu Val Arg Val Pro Arg Pro Met Lys Val Ile Asp Leu Pro
65                  70                  75                  80

Gly Gly Gly Ala Ala Phe Val Met Glu His Leu Lys Met Lys Ser Leu
                85                  90                  95

Ser Ser Gln Ala Ser Lys Leu Gly Glu Gln Met Ala Asp Leu His Leu
            100                 105                 110

Tyr Asn Gln Lys Leu Arg Glu Lys Leu Lys Glu Glu Asn Thr Val
        115                 120                 125

Gly Arg Arg Gly Glu Gly Ala Glu Pro Gln Tyr Val Asp Lys Phe Gly
130                 135                 140

Phe His Thr Val Thr Cys Cys Gly Phe Ile Pro Gln Val Asn Glu Trp
145                 150                 155                 160

Gln Asp Asp Trp Pro Thr Phe Phe Ala Arg His Arg Leu Gln Ala Gln
                165                 170                 175

Leu Asp Leu Ile Glu Lys Asp Tyr Ala Asp Arg Glu Ala Arg Glu Leu
            180                 185                 190

Trp Ser Arg Leu Gln Val Lys Ile Pro Asp Leu Phe Cys Gly Leu Glu
        195                 200                 205

Ile Val Pro Ala Leu Leu His Gly Asp Leu Trp Ser Gly Asn Val Ala
210                 215                 220

Glu Asp Asp Val Gly Pro Ile Ile Tyr Asp Pro Ala Ser Phe Tyr Gly
225                 230                 235                 240

His Ser Glu Phe Glu Leu Ala Ile Ala Leu Met Phe Gly Gly Phe Pro
                245                 250                 255

Arg Ser Phe Phe Thr Ala Tyr His Arg Lys Ile Pro Lys Ala Pro Gly
            260                 265                 270

Phe Asp Gln Arg Leu Leu Leu Tyr Gln Leu Phe Asn Tyr Leu Asn His
        275                 280                 285

Trp Asn His Phe Gly Arg Glu Tyr Arg Ser Pro Ser Leu Gly Thr Met
290                 295                 300

Arg Arg Leu Leu Lys
305

<210> SEQ ID NO 3
<211> LENGTH: 1781
<212> TYPE: DNA
<213> ORGANISM: Homo sapiens
<220> FEATURE:
<221> NAME/KEY: CDS
<222> LOCATION: (27)..(956)

<400> SEQUENCE: 3
ggcgggtccg cggccgcggc gggaac atg gag gag ctg ctg agg cgc gag ctg      53
                              Met Glu Glu Leu Leu Arg Arg Glu Leu
                                1               5 ggc tgc agc tct gtc agg gcc acg ggc cac tcg ggg ggc ggg tgc atc     101
Gly Cys Ser Ser Val Arg Ala Thr Gly His Ser Gly Gly Gly Cys Ile
 10                  15                  20                  25 agc cag ggc cgg agc tac gac acg gat caa gga cga gtg ttc gtg aaa     149
Ser Gln Gly Arg Ser Tyr Asp Thr Asp Gln Gly Arg Val Phe Val Lys
                 30                  35                  40 gtg aac ccc aag gcg gag gcc aga aga atg ttt gaa ggt gag atg gca     197
Val Asn Pro Lys Ala Glu Ala Arg Arg Met Phe Glu Gly Glu Met Ala
             45                  50                  55
```

| | | |
|---|---|---|
| agt tta act gcc atc ctg aaa aca aac acg gtg aaa gtg ccc aag ccc<br>Ser Leu Thr Ala Ile Leu Lys Thr Asn Thr Val Lys Val Pro Lys Pro<br>          60                    65                    70 | | 245 |
| atc aag gtt ctg gat gcc cca ggc ggc ggg agc gtg ctg gtg atg gag<br>Ile Lys Val Leu Asp Ala Pro Gly Gly Gly Ser Val Leu Val Met Glu<br>75                    80                    85 | | 293 |
| cac atg gac atg agg cat ctg agc agt cat gct gca aag ctt gga gcc<br>His Met Asp Met Arg His Leu Ser Ser His Ala Ala Lys Leu Gly Ala<br>90                    95                  100                105 | | 341 |
| cag ctg gcc gat tta cac ctt gat aac aag aag ctt gga gag atg cgc<br>Gln Leu Ala Asp Leu His Leu Asp Asn Lys Lys Leu Gly Glu Met Arg<br>                  110                    115                120 | | 389 |
| ctg aag gag gcg ggc aca gtg ggg aga gga ggt ggg cag gag gaa cgg<br>Leu Lys Glu Ala Gly Thr Val Gly Arg Gly Gly Gly Gln Glu Glu Arg<br>              125                    130                    135 | | 437 |
| ccc ttt gtg gcc cgg ttt gga ttt gac gtg gtg acg tgc tgt gga tac<br>Pro Phe Val Ala Arg Phe Gly Phe Asp Val Val Thr Cys Cys Gly Tyr<br>            140                    145                    150 | | 485 |
| ctc ccc cag gtg aat gac tgg cag gag gac tgg gtc gtg ttc tat gcc<br>Leu Pro Gln Val Asn Asp Trp Gln Glu Asp Trp Val Val Phe Tyr Ala<br>          155                    160                    165 | | 533 |
| cgg cag cgc att cag ccc cag atg gac atg gtg gag aag gag tct ggg<br>Arg Gln Arg Ile Gln Pro Gln Met Asp Met Val Glu Lys Glu Ser Gly<br>170                    175                    180                    185 | | 581 |
| gac agg gag gcc ctc cag ctt tgg tct gct ctg cag tta aag atc cct<br>Asp Arg Glu Ala Leu Gln Leu Trp Ser Ala Leu Gln Leu Lys Ile Pro<br>                  190                    195                200 | | 629 |
| gac ctg ttc cgt gac ctg gag atc atc cca gcc tta ctc cac ggg gac<br>Asp Leu Phe Arg Asp Leu Glu Ile Ile Pro Ala Leu Leu His Gly Asp<br>            205                    210                    215 | | 677 |
| ctc tgg ggt gga aac gta gca gag gat tcc tct ggg ccg gtg att ttt<br>Leu Trp Gly Gly Asn Val Ala Glu Asp Ser Ser Gly Pro Val Ile Phe<br>                  220                    225                230 | | 725 |
| gac cca gct tct ttc tac ggc cac tcg gaa tat gag ctg gca ata gct<br>Asp Pro Ala Ser Phe Tyr Gly His Ser Glu Tyr Glu Leu Ala Ile Ala<br>          235                    240                    245 | | 773 |
| ggc atg ttt ggg ggc ttt agc agc tcc ttt tac tcc gcc tac cac ggc<br>Gly Met Phe Gly Gly Phe Ser Ser Ser Phe Tyr Ser Ala Tyr His Gly<br>250                    255                    260                    265 | | 821 |
| aaa atc ccc aag gcc cca gga ttc gag aag cgc ctt cag ttg tat cag<br>Lys Ile Pro Lys Ala Pro Gly Phe Glu Lys Arg Leu Gln Leu Tyr Gln<br>                  270                    275                280 | | 869 |
| ctc ttt cac tac ttg aac cac tgg aat cat ttt gga tcg ggg tac aga<br>Leu Phe His Tyr Leu Asn His Trp Asn His Phe Gly Ser Gly Tyr Arg<br>            285                    290                    295 | | 917 |
| gga tcc tcc ctg aac atc atg agg aat ctg gtc aag tga gcgggcctta<br>Gly Ser Ser Leu Asn Ile Met Arg Asn Leu Val Lys<br>          300                    305 | | 966 |
| ctctggaagg aggcctcaga ggtttctcca cagtcctctt ctgggcaaat tcttgtttct | | 1026 |
| tcacatgccg gactagctta agaccaatgc agtagcttat ttccaagcct tgcaaagtat | | 1086 |
| ataatatcta agaggaaagg ttttgtcatc ccagcgttgt ccactttgtg ggctttgta | | 1146 |
| ggtagacgga gccacactac aggcagggta tgagcagagg gatgtatgga gtgtgggtga | | 1206 |
| ctctgagcct cactgctgct gcaaggtggg gaaactgtaa gtgaaccct gtgggtgcgg | | 1266 |
| gggagggtat ccggtgcaca gggaggtggc cagcgccccc gggcactgct gctcataggt | | 1326 |
| acctttccgc tgcctcctcc ctgctctcct gtgcaggaat gtctctgagc tgttcacgtt | | 1386 |
| gatgcttctt ggttggcaag acttgggtgt agatatgaaa ccatcttact aaaagcgtct | | 1446 |

-continued

```
taaaatgacc aattccagaa tcaagcgtat tccgttttct tcctgcatga tcctgggccc   1506
tcccgcaggc tgagcaagtc tgtaaactga ttctgggaga aaccaagctg ctggccgtag   1566
ggtgtccttg gtacatcca ggagtcttca ttgcttctgt tattaccccg tctcctctgc   1626
cattttctac agcttgctga gttgtcattc ctttgcaaca ttaaaataca tgctgaactc   1686 atattttttcc ttccttcact gttgtagtaa agagacatat ttcatgaatg gcattgatgc   1746 taataaaatcc tttgcacaaa aaaaaaaaaa aaaaa                              1781
```

<210> SEQ ID NO 4
<211> LENGTH: 309
<212> TYPE: PRT
<213> ORGANISM: Homo sapiens

<400> SEQUENCE: 4

```
Met Glu Glu Leu Leu Arg Arg Glu Leu Gly Cys Ser Ser Val Arg Ala
1               5                   10                  15

Thr Gly His Ser Gly Gly Cys Ile Ser Gln Gly Arg Ser Tyr Asp
                20                  25                  30

Thr Asp Gln Gly Arg Val Phe Val Lys Val Asn Pro Lys Ala Glu Ala
            35                  40                  45

Arg Arg Met Phe Glu Gly Glu Met Ala Ser Leu Thr Ala Ile Leu Lys
        50                  55                  60

Thr Asn Thr Val Lys Val Pro Lys Pro Ile Lys Val Leu Asp Ala Pro
65                  70                  75                  80

Gly Gly Gly Ser Val Leu Val Met Glu His Met Asp Met Arg His Leu
                85                  90                  95

Ser Ser His Ala Ala Lys Leu Gly Ala Gln Leu Ala Asp Leu His Leu
            100                 105                 110

Asp Asn Lys Lys Leu Gly Glu Met Arg Leu Lys Glu Ala Gly Thr Val
        115                 120                 125

Gly Arg Gly Gly Gly Gln Glu Glu Arg Pro Phe Val Ala Arg Phe Gly
    130                 135                 140

Phe Asp Val Val Thr Cys Cys Gly Tyr Leu Pro Gln Val Asn Asp Trp
145                 150                 155                 160

Gln Glu Asp Trp Val Val Phe Tyr Ala Arg Gln Arg Ile Gln Pro Gln
                165                 170                 175

Met Asp Met Val Glu Lys Glu Ser Gly Asp Arg Glu Ala Leu Gln Leu
            180                 185                 190

Trp Ser Ala Leu Gln Leu Lys Ile Pro Asp Leu Phe Arg Asp Leu Glu
        195                 200                 205

Ile Ile Pro Ala Leu Leu His Gly Asp Leu Trp Gly Gly Asn Val Ala
    210                 215                 220

Glu Asp Ser Ser Gly Pro Val Ile Phe Asp Pro Ala Ser Phe Tyr Gly
225                 230                 235                 240

His Ser Glu Tyr Glu Leu Ala Ile Ala Gly Met Phe Gly Gly Phe Ser
                245                 250                 255

Ser Ser Phe Tyr Ser Ala Tyr His Gly Lys Ile Pro Lys Ala Pro Gly
            260                 265                 270

Phe Glu Lys Arg Leu Gln Leu Tyr Gln Leu Phe His Tyr Leu Asn His
        275                 280                 285

Trp Asn His Phe Gly Ser Gly Tyr Arg Gly Ser Ser Leu Asn Ile Met
    290                 295                 300

Arg Asn Leu Val Lys
305
```

```
<210> SEQ ID NO 5
<211> LENGTH: 30
<212> TYPE: DNA
<213> ORGANISM: Homo sapiens

<400> SEQUENCE: 5
atggagcagc tgctgcgcgc cgagctgcgc                                    30

<210> SEQ ID NO 6
<211> LENGTH: 30
<212> TYPE: DNA
<213> ORGANISM: Homo sapiens

<400> SEQUENCE: 6
ctacttgagc agccttcgca tggtgcccaa                                    30

<210> SEQ ID NO 7
<211> LENGTH: 40
<212> TYPE: DNA
<213> ORGANISM: Artificial Sequence
<220> FEATURE:
<223> OTHER INFORMATION: PCR primer for amplyfying FN3KRP cDNA

<400> SEQUENCE: 7
ataagaatgc ggccgccacc atggaggagc tgctgaggcg                         40

<210> SEQ ID NO 8
<211> LENGTH: 37
<212> TYPE: DNA
<213> ORGANISM: Artificial Sequence
<220> FEATURE:
<223> OTHER INFORMATION: PCR primer for amplifying FN3KRP cDNA

<400> SEQUENCE: 8
atagtttagc ggccgctcac ttgaccagat tcctcat                            37
```

DRUG-PHOSPHORYLATING ENZYME

CROSS-REFERENCES TO RELATED APPLICATIONS

This application is the National Stage of International Application No. PCT/JP2007/065232, filed Aug. 3, 2007, which claims priority from Japanese Application No. 2006-213734, filed Aug. 4, 2006, each application is incorporated herein by reference in its entirety.

TECHNICAL FIELD

The present invention relates to an enzyme that phosphorylates a drug in the living body. Moreover, the present invention relates to a method of screening for a compound phosphorylated by the aforementioned enzyme, a method of determining the ability of a subject to phosphorylate a test compound, etc.

BACKGROUND ART

Some pharmaceuticals at the stage of being administered to patients have a structure different from that of a compound having actual drug efficacy. After such pharmaceuticals have been administered to a patient, they are metabolized in the living body. As a result, their structure is changed, and they exhibit their drug efficacy at that time. Such a compound before being metabolized in the living body is called a pro-drug. Various types of enzymes that metabolize a prodrug to a compound having drug efficacy have been known.

Some amino alcohol derivatives are phosphorylated in vivo and, as a result, exhibit immunosuppressive activity. For example, FTY720 (2-Amino-2-[2-(4-octylphenyl)ethyl]propane-1,3-diol hydrochloride) is phosphorylated in vivo by sphingosine kinase 1 and 2, so that it can be converted to FTY720-phosphate [i.e., (:)2-amino-2 phosphoryloxymethyl-4-(4-octylphenyl)butanol] exhibiting immunosuppressive action (The Journal of Biological Chemistry, (2003), 278, p. 47408-47415).

On the other hand, it is also considered that a compound represented by general formula (I) (wherein each of $R^1$ and $R^2$ represents a hydrogen atom; $R^3$ represents a C1-C6 alkyl group or a hydroxymethyl group; $R^4$ represents a hydrogen atom, a halogen atom or a C1-C6 alkyl group; $R^5$ represents a phenyl group, which is substituted with 1 to 3 substituents selected from the group consisting of a hydrogen atom, a halogen atom, a cyano group, a C1-C6 alkyl group, a C1-C6 alkoxy group, a C3-C6 cycloalkyl group, a halogeno C1-C6 alkyl group, a phenyl group and a benzyloxy group, a halogen atom or a hydrogen atom; X represents a vinylene group (CH=CH group), an oxygen atom, a sulfur atom or a methylamino group; Y represents a single bond, an oxygen atom, a sulfur atom or a carbonyl group; Z represents a single bond or a C1-C8 alkylene group; and n is 2 or 3) is phosphorylated in vivo, so that it can be converted to an active form exhibiting immunosuppressive activity (Japanese Patent Laid-Open No. 2005-46141). However, the mechanism of this phosphorylation in vivo is unknown.

Elucidation of the mechanism of phosphorylation of such compounds has been considered effective for the search for compounds that are activated by being phosphorylated in vivo, for clarification of the mechanism for expression of activity, for selection of a patient who is sensitive to a drug, etc.

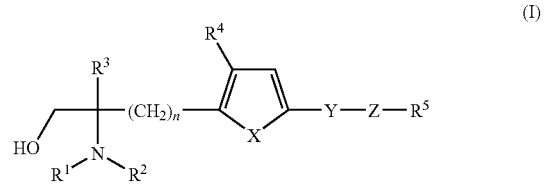

It has been reported that a human fructosamine-3-kinase-related protein (which is hereinafter also referred to as "human FN3KRP") has activity of phosphorylating position 3 of ketosamines such as ribulosamine or psicosamine (Diabetes, (2003), 52, p. 2888-2895). However, the role of such human fructosamine-3-kinase-related protein in vivo is unknown.

As a result of intensive studies directed towards elucidating the phosphorylation mechanism thereof in vivo, the present inventor has found that the protein known as human FN3KRP or human fructosamine-3-kinase (which is hereinafter also referred to as "human FN3K") is associated with phosphorylation of the compound represented by the aforementioned general formula (I), thereby completing the present invention.

It is an object of the present invention to elucidate an enzyme that phosphorylates in vivo the compound represented by the aforementioned general formula (I), such as (2R)-2-amino-2-methyl-4-[5-(5-phenylpentanoyl)thiophen-2-yl]butan-1-ol. In addition, it is another object of the present invention to provide a method of phosphorylating the aforementioned compound using an enzyme that phosphorylates it. Moreover, it is a further object of the present invention to provide a method of screening for a compound phosphorylated by the aforementioned enzyme. Furthermore, it is a further object of the present invention to provide a method of determining the ability of a subject to phosphorylate a test compound.

DISCLOSURE OF THE INVENTION

Problems to be Solved by the Invention

As a result of intensive studies directed towards achieving the aforementioned objects, the present inventors have found that an enzyme that phosphorylates the compound represented by the aforementioned general formula (I), such as (2R)-2-amino-2-methyl-4-[5-(5-phenylpentanoyl)thiophen-2-yl]butan-1-ol, is the protein known as fructosamine-3-kinase-related protein (which is hereinafter also referred to as "FN3KRP") and/or fructosamine-3-kinase (which is hereinafter also referred to as "FN3K"), thereby completing the present invention.

Means for Solving the Problems

That is to say, the present invention has the following features [1] to [13].

[1] A method of screening for a substance phosphorylated by human FN3KRP and/or human FN3K, which comprises the following steps (1) to (3):
(1) contacting a test substance with a polypeptide selected from the group consisting of the following (a) to (c):
  (a) a polypeptide having the amino acid sequence of amino acid Nos. 1-309 of SEQ ID NO: 2 in the sequence listing;
  (b) a polypeptide having the amino acid sequence of amino acid Nos. 1-309 of SEQ ID NO: 4 in the sequence listing; and (c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol;
(2) measuring the amount of phosphoric ester of the test substance generated; and
(3) comparing the amount of the generated phosphoric ester measured in (2) above with the amount of the phosphoric ester of the test substance measured when the test substance is not contacted with the polypeptide selected from the above (a) to (c).

[2] A method of screening for a substance phosphorylated by human FN3KRP and/or human FN3K, which comprises the following steps (1) to (4):
(1) contacting a test substance with a polypeptide selected from the group consisting of the following (a) to (c):
 (a) a polypeptide having the amino acid sequence of amino acid Nos. 1-309 of SEQ ID NO: 2 in the sequence listing;
 (b) a polypeptide having the amino acid sequence of amino acid Nos. 1-309 of SEQ ID NO: 4 in the sequence listing; and
 (c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol;
(2) measuring the amount of phosphoric ester of the test substance generated;
(3) comparing the amount of the generated phosphoric ester measured in (2) above with the amount of the phosphoric ester of the test substance measured when the test substance is not contacted with the polypeptide selected from the above (a) to (c); and
(4) determining that the test substance has been phosphorylated, when the amount of the phosphoric ester measured in (2) above is greater compared with the amount of the phosphoric ester of the test substance measured when the test substance is not contacted with the polypeptide selected from the above (a) to (c).

[3] A method of screening for a substance having immunosuppressive activity, which comprises the following steps (1) to (3):
(1) contacting a test substance with a polypeptide selected from the group consisting of the following (a) to (c):
 (a) a polypeptide having the amino acid sequence of amino acid Nos. 1-309 of SEQ ID NO: 2 in the sequence listing;
 (b) a polypeptide having the amino acid sequence of amino acid Nos. 1-309 of SEQ ID NO: 4 in the sequence listing; and
 (c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol;
(2) measuring the amount of phosphoric ester of the test substance generated; and
(3) comparing the amount of the generated phosphoric ester measured in (2) above with the amount of the phosphoric ester of the test substance measured when the test substance is not contacted with the polypeptide selected from the above (a) to (c).

[4] A method of screening for a substance having immunosuppressive activity, which comprises the following steps (1) to (4):
(1) contacting a test substance with a polypeptide selected from the group consisting of the following (a) to (c):
 (a) a polypeptide having the amino acid sequence of amino acid Nos. 1-309 of SEQ ID NO: 2 in the sequence listing;
 (b) a polypeptide having the amino acid sequence of amino acid Nos. 1-309 of SEQ ID NO: 4 in the sequence listing; and
 (c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol;
(2) measuring the amount of phosphoric ester of the test substance generated;
(3) comparing the amount of the generated phosphoric ester measured in (2) above with the amount of the phosphoric ester of the test substance measured when the test substance is not contacted with the polypeptide selected from the above (a) to (c); and
(4) determining that the test substance has been phosphorylated, when the amount of the phosphoric ester measured in (2) above is greater compared with the amount of the phosphoric ester of the test substance measured when the test substance is not contacted with the polypeptide selected from the above (a) to (c).

[5] The screening method according to any one of [1] to [4] above, characterized in that the test substance is a compound represented by the following general formula (I):

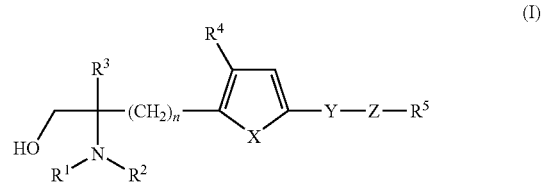

wherein each of $R^1$ and $R^2$ represents a hydrogen atom; $R^3$ represents a C1-C6 alkyl group or a hydroxymethyl group; $R^4$ represents a hydrogen atom, a halogen atom or a C1-C6 alkyl group; $R^5$ represents a phenyl group, a phenyl group which is substituted with 1 to 3 substituents selected from the group consisting of a halogen atom, a cyano group, a C1-C6 alkyl group a C1-C6 alkoxy group, a C3-C6 cycloalkyl group, a halogeno C1-C6 alkyl group, a phenyl group and a benzyloxy group, a halogen atom or a hydrogen atom; X represents a vinylene group (CH=CH group), an oxygen atom, a sulfur atom or a methylamino group; Y represents a single bond, an oxygen atom, a sulfur atom or a carbonyl group; Z represents a single bond or a C1-C8 alkylene group; and n is 2 or 3.

Construction of human FN3K and/or human FN3KRP expression vector

[6] A method of producing a phosphoric ester, which comprises the following steps (1) and (2):
(1) contacting the compound represented by general formula (I) with a polypeptide selected from the group consisting of the following (a) to (c):
 (a) a polypeptide having the amino acid sequence of amino acid Nos. 1-309 of SEQ ID NO: 2 in the sequence listing;
 (b) a polypeptide having the amino acid sequence of amino acid Nos. 1-309 of SEQ ID NO: 4 in the sequence listing; and
 (c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol; and
(2) obtaining the phosphoric ester of the compound represented by general formula (I) from the reaction solution in (1) above.

[7] A method of determining the ability of a subject to generate the phosphoric ester of the compound represented by general formula (I), which comprises the following steps (1) to (3):
(1) extracting total RNA from a sample collected from a subject;
(2) measuring the expression level of a polynucleotide selected from the group consisting of the following (a) to (c) in the total RNA:
(a) a polynucleotide having the nucleotide sequence consisting of nucleotide Nos. 6-935 of SEQ ID NO: 1 in the sequence listing;
(b) a polynucleotide having the nucleotide sequence consisting of nucleotide Nos. 27-956 of SEQ ID NO: 3 in the sequence listing; and
(c) a polynucleotide hybridizing under stringent conditions with a polynucleotide having the nucleotide sequence complementary to the nucleotide sequence described in (a) or (b) above, and encoding a polypeptide having the ability to phosphorylate in vivo the compound represented by general formula (I); and
(3) comparing the expression level of the polynucleotide measured in (2) above with the expression level of the above described polynucleotide in a sample that has been confirmed as having the ability to phosphorylate in vivo the compound represented by general formula (I), so as to examine the ability of the subject to phosphorylate the compound represented by general formula (I).

[8] A method of determining the ability of a patient to generate the phosphoric ester of the compound represented by general formula (I), which comprises the following steps (1) and (2):
(1) measuring the expression level of a polypeptide selected from the group consisting of the following (a) to (c) in a sample collected from a subject:
(a) a polypeptide having the amino acid sequence of amino acid Nos. 1-309 of SEQ ID NO: 2 in the sequence listing;
(b) a polypeptide having the amino acid sequence of amino acid Nos. 1-309 of SEQ ID NO: 4 in the sequence listing; and
(c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol; and
(2) comparing the expression level of the polypeptide measured in (1) above with the expression level of the above described polypeptide in a sample that has been confirmed as having the ability to phosphorylate in vivo the compound represented by general formula (I), so as to examine the ability of the subject to phosphorylate the compound represented by general formula (I).

[9] A method of determining the ability of a patient to generate the phosphoric ester of the compound represented by general formula (I), which comprises the following steps (1) and (2):
(1) measuring the enzyme activity of a polypeptide selected from the group consisting of the following (a) to (c) in a sample collected from a subject:
(a) a polypeptide having the amino acid sequence of amino acid Nos. 1-309 of SEQ ID NO: 2 in the sequence listing;
(b) a polypeptide having the amino acid sequence of amino acid Nos. 1-309 of SEQ ID NO: 4 in the sequence listing; and
(c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol; and
(2) comparing the enzyme activity of the polypeptide measured in (1) above with the enzyme activity of the above described polypeptide in a sample that has been confirmed as having the ability to phosphorylate in vivo the compound represented by general formula (I), so as to examine the ability of the subject to phosphorylate the compound represented by general formula (I).

[10] A method of determining the ability of a subject to generate the phosphoric ester of the compound represented by general formula (I), which comprises the following steps (1) to (3):
(1) examining the nucleotide sequence of a polynucleotide selected from the group consisting of the following (a) to (c) in a sample collected from a subject:
(a) a polynucleotide having the nucleotide sequence consisting of nucleotide Nos. 1-1466 of SEQ ID NO: 1 in the sequence listing;
(b) a polynucleotide having the nucleotide sequence consisting of nucleotide Nos. 1-1781 of SEQ ID NO: 3 in the sequence listing; and
(c) a polynucleotide hybridizing under stringent conditions with a polynucleotide having a nucleotide sequence complementary to the nucleotide sequence described in (a) or (b) above, and encoding a polypeptide having the ability to phosphorylate in vivo the compound represented by general formula (I);
(2) examining the presence or absence of a mutation in the nucleotide sequence of the above described polynucleotide that influences enzyme activity; and
(3) determining that the subject has only a low ability to phosphorylate the compound represented by general formula (I) when the subject has, in the nucleotide sequence, a mutation that decreases the phosphorylating activity of the polypeptide encoded by the above described polynucleotide, and determining that the subject has the ability to phosphorylate the compound represented by general formula (I) when the subject does not have, in the nucleotide sequence, a mutation that decreases the phosphorylating activity of the above described polypeptide.

[11] A method of identifying, in a nucleotide sequence, a mutation that influences on the phosphorylating activity of a polypeptide encoded by a polynucleotide selected from the group consisting of the following (a) to (c):
(a) a polynucleotide having the nucleotide sequence consisting of nucleotide Nos. 1-1466 of SEQ ID NO: 1 in the sequence listing;
(b) a polynucleotide having the nucleotide sequence consisting of nucleotide Nos. 1-1781 of SEQ ID NO: 3 in the sequence listing; and
(c) a polynucleotide hybridizing under stringent conditions with a polynucleotide having a nucleotide sequence complementary to the nucleotide sequence described in (a) or (b) above, and encoding a polypeptide having the ability to phosphorylate in vivo the compound represented by general formula (I),
the above described method comprising the following steps (1) to (3):

(1) examining the nucleotide sequence of a polynucleotide selected from the group consisting of the above (a) to (c) in a sample collected from a subject;
(2) examining the presence or absence of a mutation in the nucleotide sequence of the above described polynucleotide; and
(3) examining the relationship between the above described mutation in the nucleotide sequence of the above described polynucleotide and the phosphorylating activity of the polypeptide encoded by the above described polynucleotide, so as to identify in the nucleotide sequence of the polynucleotide a mutation that influences the phosphorylating activity.

[12] The method according to any one of [7] to [11] above, characterized in that the sample is peripheral blood.

[13] A kit for diagnosing ability to metabolize a drug, which comprises at least one selected from the group consisting of the following (1) to (5):
(1) an oligonucleotide primer comprising 15 to 30 contiguous nucleotides that is used for specifically amplifying a part of or the entire polynucleotide having the nucleotide sequence as shown in SEQ ID NO: 1 or 3 in the sequence listing;
(2) a polynucleotide probe comprising 15 or more contiguous nucleotides that hybridizes under stringent conditions with the polynucleotide having the nucleotide sequence as shown in SEQ ID NO: 1 or 3 in the sequence listing, for detecting the above described polynucleotide;
(3) a solid-phase sample having a polynucleotide selected from either the oligonucleotide primer described in (1) above or the polynucleotide probe described in (2) above immobilized thereon;
(4) an antibody that specifically binds to a polypeptide selected from the following (a) to (c), so as to detect the protein:
(a) a polypeptide having the amino acid sequence of amino acid Nos. 1-309 of SEQ ID NO: 2 in the sequence listing;
(b) a polypeptide having the amino acid sequence of amino acid Nos. 1-309 of SEQ ID NO: 4 in the sequence listing; and
(c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol; and
(5) a secondary antibody that binds to the antibody described in (4) above.

ADVANTAGES OF THE INVENTION

The present invention is able to provide a method of phosphorylating the aforementioned compound using a human fructosamine-3-kinase-related protein (which is hereinafter also referred to as "human FN3KRP") and/or human fructosamine-3-kinase (which is hereinafter also referred to as "human FN3K"). Moreover, the present invention is able to provide a method of screening for a compound phosphorylated by the aforementioned enzyme. Furthermore, the present invention is able to provide a method of determining the ability of a subject to phosphorylate a test compound.

BEST MODE FOR CARRYING OUT THE INVENTION

1. Definition
The term "gene" is used in the present specification to include not only DNA but also its mRNA, cDNA and its cRNA. In addition, the term "polynucleotide" is used in the present specification to have the same meaning as that of a nucleic acid. Thus, the term "polynucleotide" includes DNA, RNA, a probe, an oligonucleotide, and a primer. The terms "polypeptide" and "protein" are used with no distinctions in the present specification. Moreover, the term "RNA fraction" is used in the present specification to mean a fraction containing RNA. Furthermore, the term "cell" is used in the present specification to include the cell of an individual animal and a cultured cell. The term "total RNA fraction" is used in the present specification to mean a fraction that contains total RNA. This is, a fraction that contains total RNA extracted from blood, various types of organs, various types of tissues, cultured cells, etc. by an ordinary method such as the use of a solvent for RNA extraction. The expression "hybridize under stringent conditions" is used in the present specification to mean: conditions wherein identification can be carried out by hybridization performed at 68° C. in a commercially available hybridization solution, ExpressHyb Hybridization Solution (manufactured by Clontech); conditions wherein identification can be carried out by hybridization performed at 68° C. using a DNA-immobilized filter in the presence of 0.7-1.0 M NaCl and the subsequent washing of the resultant at 68° C. with an SSC solution in a 0.1-2 times concentration (1 time concentration SSC consists of 150 mM NaCl and 15 mM sodium citrate); or conditions equivalent thereto.

2. Human FN3KRP and Human FN3K
The human fructosamine-3-kinase (human FN3K) or human fructosamine-3-kinase-related protein (human FN3KRP) that can be used in the present invention is not limited to an entire-length protein. A partial peptide consisting of a partial sequence of the entire-length protein may also be used, as long as it enables the phosphorylation reaction of a compound that can be used in the present invention. Moreover, a natural protein obtained from human-derived cells, or a protein obtained from cells that have been genetically modified to express the aforementioned protein using a gene cloned by the PCR method or the like, may also be used. Furthermore, such proteins may be purified or may be partially purified.

The nucleotide sequence of cDNA of human FN3K is as shown in nucleotide Nos. 1-1466 of SEQ ID NO: 1 in the sequence listing, for example. In addition, the amino acid sequence of human FN3K is as shown in amino acid Nos. 1-309 of SEQ ID NO: 2 in the sequence listing, for example. The nucleotide sequence of cDNA of human FN3K has been registered in GenBank under accession No. NM_022158.

On the other hand, the nucleotide sequence of cDNA of human FN3KRP is as shown in nucleotide Nos. 1-1781 of SEQ ID NO: 3 in the sequence listing, for example. In addition, the amino acid sequence of human FN3KRP is as shown in amino acid Nos. 1-309 of SEQ ID NO: 4 in the sequence listing, for example. The nucleotide sequence of cDNA of human FN3KRP has been registered in GenBank under accession No. NM_024619.

In the present specification, the term "human FN3K gene" is used to mean a gene having a nucleotide sequence consisting of nucleotide Nos. 6-935 of SEQ ID NO: 1 in the sequence listing, or a gene that hybridizes under stringent conditions with a polynucleotide having a nucleotide sequence complementary to the gene having the aforementioned nucleotide sequence and that has a nucleotide sequence encoding a protein having the same level of biological activity as that of human FN3K.

In the present specification, the term "human FN3K" is used to mean a protein having the amino acid sequence of amino acid Nos. 1-309 of SEQ ID NO: 2 in the sequence listing, or a protein that has an amino acid sequence comprising a deletion, substitution or addition of one or several amino acids with respect to the amino acid sequence of the aforementioned protein and that has the same level of biological activity as that of human FN3K.

In the present specification, the term "human FN3KRP gene" is used to mean a gene having the nucleotide sequence consisting of nucleotide Nos. 27-956 of SEQ ID NO: 3 in the sequence listing, or a gene that hybridizes under stringent conditions with a polynucleotide having a nucleotide sequence complementary to the gene having the aforementioned nucleotide sequence and that has a nucleotide sequence encoding a protein having the same level of biological activity as that of human FN3KRP. In the present specification, the term "human FN3KRP" is used to mean a protein having the amino acid sequence of amino acid Nos. 1-309 of SEQ ID NO: 4 in the sequence listing, or a protein that has an amino acid sequence comprising a deletion, substitution or addition of one or several amino acids with respect to the amino acid sequence of the aforementioned protein and that has the same level of biological activity as that of human FN3KRP.

A fusion protein formed by adding another amino acid sequence to human FN3K, human FN3KRP or a partial peptide thereof is also included in the human FN3K, the human FN3KRP, and the partial peptide thereof. Such fusion proteins include a histidine tag-fused protein, a FLAG-fused protein, and a fluorochrome-fused protein such as GFP, but examples are not limited thereto.

The enzyme activity of human FN3K and/or human FN3KRP can be measured by incubating such human FN3K and/or human FN3KRP, and a substance used as a substrate in a suitable buffer, and then assaying a phosphorylated compound as a product. For example, human FN3K and/or human FN3KRP are incubated with (2R)-2-amino-2-methyl-4-[5-(5-phenylpentanoyl)thiophen-2-yl]butan-1-ol, and the phosphoric ester generated is then assayed by HPLC, so that the enzyme activity of the human FN3K and/or human FN3KRP can be measured.

3. Obtainment of Human FN3K cDNA and Human FN3KRP cDNA (1) Human FN3K cDNA

A commercially available product can be used as human FN3K cDNA. Such a commercially available product can be obtained from GeneCopoeia (catalog No. GC-W 1392), for example.

Alternatively, human FN3K cDNA can be obtained by the following procedures using a cDNA library including a human FN3K gene.

Full-length cDNA is obtained from a cDNA library, in which a human FN3K gene has been expressed, in accordance with a known method such as colony hybridization. Using this full-length cDNA as a template, PCR is performed to obtain human FN3K cDNA. As a cDNA library, a human bone marrow-derived cDNA library can be used, for example. Alternatively, Creator SMART Human cDNA Libraries (Clontech) can be used as a commercially available human cDNA library, or a cDNA library can be prepared independently.

Moreover, it is also possible to perform PCR directly using a cDNA library as a template, without conducting colony hybridization, so as to obtain human FN3K cDNA.

Any types of PCR primers can be used, as long as they are able to amplify human FN3K cDNA. Thus, suitable primers can be selected by a known method. As primers used in PCR for amplifying human FN3K cDNA, oligonucleotides having the following nucleotide sequences can be selected, for example:

(primer 1: SEQ ID NO: 5 in the sequence listing)
5'-atggagcagctgctgcgcgccgagctgcgc-3';
and (primer 2: SEQ ID NO: 6 in the sequence listing)
5'-ctacttgagcagccttcgcatggtgcccaa-3'.

(2) Human FN3KRP cDNA

Full-length cDNA is obtained from a cDNA library, in which a human FN3KRP gene has been expressed, in accordance with a known method such as colony hybridization. Using this full-length cDNA as a template, PCR is performed to obtain human FN3KRP cDNA. As a cDNA library, a human bone marrow-derived cDNA library can be used, for example. As a commercially available human cDNA library, Creator SMART Human cDNA Libraries (Clontech) can be used, or a cDNA library can also be prepared independently.

Moreover, it is also possible to perform PCR directly using a cDNA library as a template, so as to obtain human FN3KRP cDNA.

Any types of PCR primers can be used, as long as they are able to amplify human FN3KRP cDNA. Thus, suitable primers can be selected by a known method. As primers used in PCR for amplifying human FN3KRP cDNA, oligonucleotides having the following nucleotide sequences can be selected, for example:

(primer 3: SEQ ID NO: 7 in the sequence listing)
5'-ataagaatgcggccgccaccatggaggagctgctgaggcg-3';
and (primer 4: SEQ ID NO: 8 in the sequence listing)
5'-atagtttagcggccgctcacttgaccagattcctcat-3'.

It is to be noted that persons skilled in the technical field, to which the present invention pertains, are able to carry out modification of a portion of the naturally-occurring-type nucleotide sequence of a human FN3K gene and/or a human FN3KRP gene, such as substitution of the portion with other nucleotides, deletion of the portion, or addition of other nucleotides thereto, so as to prepare a polynucleotide having the same level of biological activity as that of the naturally-occurring-type human FN3K gene and/or human FN3KRP gene. Thus, a polynucleotide that has a nucleotide sequence comprising a substitution, deletion or addition of nucleotides with respect to the naturally-occurring-type nucleotide sequence and that exhibits the same level of biological activity as that of the naturally-occurring-type human FN3K gene and/or human FN3KRP gene can also be used in the present invention. Such modification of a nucleotide sequence can be carried out by methods such as introduction of deletion using restriction enzymes or DNA exonuclease, mutagenesis such as site-directed mutagenesis, modification of a nucleotide sequence by the PCR method using mutant primers, or direct introduction of synthetic mutant DNA. In addition, a polynucleotide that hybridizes under stringent conditions with a polynucleotide having a nucleotide sequence complementary to the human FN3K gene or human FN3KRP gene and that has the same level of biological activity as that of human FN3K or human FN3KRP can also be used.

4. Expression of Human FN3K and/or Human FN3KRP

Construction of human FN3K and/or human FN3KRP expression vector

Human FN3K and/or human FN3KRP can be produced by synthesizing them in vitro, or by allowing host cells to generate them according to genetic manipulation. Specifically, a human FN3K gene and/or a human FN3KRP gene is incorporated into a vector capable of expressing the human FN3K gene and/or the human FN3KRP gene. Thereafter, the human FN3K and/or human FN3KRP is synthesized in a solution that contains an enzyme, a substrate and an energetic material necessary for transcription and translation. Alternatively, host cells of prokaryotes or eukaryotes are transformed, and they are thereby allowed to express human FN3K and/or human FN3KRP, so as to obtain the human FN3K and/or the human FN3KRP.

Examples of a prokaryotic host include *Escherichia coli* and *Bacillus subtilis*. In order to transform host cells with a gene of interest, host cells are transformed with a plasmid vector that contains a replicon derived from species compatible with the host, namely, a replication origin, and a regulatory sequence. Moreover, the vector preferably has a sequence capable of imparting the selectivity of a phenotypic character (phenotype) to cells to be transformed.

Examples of *Escherichia coli* that is commonly used herein include a K12 strain and a DH5α strain. Examples of a vector that is commonly used herein include plasmids such as pBR322, or pUC series, pcDNA3.1(+) (Invitrogen). However, the *Escherichia coli* and vectors are not limited thereto, and various types of known strains and vectors can be used.

A preferred example of *Bacillus subtilis* is a 207-25 strain. As a vector, pTUB228 (Ohmura, K. et al., (1984) J. Biochem. 95, 87-93) and the like can be used, but examples are not limited thereto. Ligation of a DNA sequence encoding the signal peptide sequence of the α-amylase of *Bacillus subtilis* enables secretion and expression outside the cell mass.

Eukaryotic cells used as host cells include the cells of vertebrate animals, insects, yeasts, etc. Vertebrate animal cells that are commonly used herein include COS cells as monkey cells (Gluzman, Y. (1981) Cell 23, 175-182, ATCC: CRL-1650) and dihydrofolate reductase-deficient cell lines of Chinese hamster ovary cells (CHO cells; ATCC: CCL-61) (Urlaub, G. and Chasin, L. A. (1980) Proc. Natl. Acad. Sci. USA 77, 4126-4220), but examples are not limited thereto.

When HEK293 cell are used as host cells, for example, pcDNA3.2-DEST (Invitrogen) can be used as a vector.

The thus obtained transformant can be cultured according to an ordinary method. By such culture, a polypeptide of interest can be generated inside or outside the cells. As a medium used in the culture, various types of media that are commonly used depending on the types of the host cells used can be selected, as appropriate. For example, in the case of the aforementioned HEK293 cells, a medium formed by adding, as necessary, a serum component such as fetal bovine serum to an RPMI1640 medium or Dulbecco's Modified Eagle's Medium, can be used.

A recombinant protein generated inside or outside the cells of a transformant as a result of the aforementioned culture can be separated and purified by various types of known separation operation methods that utilize physical or chemical properties of the protein. Specific examples of such separation operation methods include a treatment using a common protein precipitant, ultrafiltration, various types of liquid chromatography such as molecular sieve chromatography (gel filtration), adsorption chromatography, ion exchange chromatography, affinity chromatography or high performance liquid chromatography (HPLC), dialysis, and combinations thereof. In addition, by connecting histidine consisting of 6 residues with a recombinant protein to be expressed, the protein can be efficiently purified using a nickel affinity column. By combining the aforementioned methods, the polypeptide of the present invention can easily be produced in large amounts at high yield and at high purity. Moreover, the molecular weight of the purified polypeptide can be determined by an ordinary method such as mass spectrometry or SDS-PAGE.

Enzyme activity is used as an indicator for purification of human FN3K and/or human FN3KRP.

5. Compound Phosphorylated by Phosphorylating Enzyme

The type of a compound that can be used as a substrate of human FN3K and/or human FN3KRP in the present invention is not particularly limited, as long as it is phosphorylated by the human FN3K and/or the human FN3KRP. An example is a compound represented by the following general formula (I):

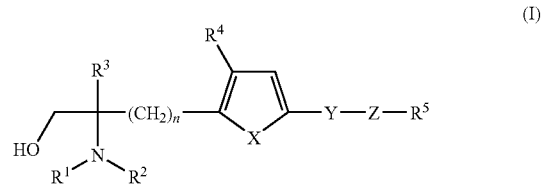

Amino alcohol derivatives represented by the above general formula (I) can be produced according to the methods described, for example, in International Publication WO94/08943 pamphlet (FTY720), International Publication WO96/06068 pamphlet (an FTY analogous compound), International Publication WO98/45249 pamphlet (an FTY analogous compound), International Publication WO03/029184 pamphlet (ROX-2127; a KRP-203 analogous compound), International Publication WO03/029205 pamphlet (KRP-203), International Publication WO02/06268 pamphlet (a thiophene derivative), International Publication WO03/059880 pamphlet (a pyrrole derivative), International Publication WO05/005383 pamphlet (a substituted pyrrole derivative), International Publication WO05/063671 pamphlet (an ether derivative of a benzene ring), etc.

Preferred substituents, which are used when such amino alcohol derivative represented by the above general formula (I) of the present invention is used as an active ingredient of a pharmaceutical composition, will be shown below.

Each of $R^1$ and $R^2$ is preferably a hydrogen atom.

$R^3$ is preferably a C1-C6 alkyl group or a hydroxymethyl group, and more preferably a methyl group or a hydroxymethyl group.

$R^4$ is preferably a hydrogen atom, a halogen atom or a C1-C6 alkyl group, more preferably a hydrogen atom, a chlorine atom or a methyl group, and particularly preferably a hydrogen atom or a chlorine atom.

$R^5$ is, for example, a phenyl group, a phenyl group which is substituted with 1 to 3 substituents selected from the group consisting of a halogen atom, a cyano group, a C1-C6 alkyl group, a C1-C6 alkoxy group, a C3-C6 cycloalkyl group, a halogeno C1-C6 alkyl group, a phenyl group and a benzyloxy group, a halogen atom or a hydrogen atom; preferably, a phenyl group, a phenyl group which is substituted with 1 to 3 substituents selected from the group consisting of a fluorine atom, a chlorine atom, a cyano group, a methyl group, a methoxy group, a cyclopropyl group, a trifluoromethyl group, a phenyl group and a benzyloxy group, a fluorine atom or a hydrogen atom; more preferably, a phenyl group, a phenyl group which is substituted with 1 to 3 substituents selected from the group consisting of a methyl group, a methoxy group, a trifluoromethyl group, a phenyl group and a benzyloxy group, a fluorine atom or a hydrogen atom; and particularly preferably, a phenyl group, a 4-methylphenyl group, a 4-methoxyphenyl group, a 3-methoxy-4-methylphenyl group, a 3-trifluoromethylphenyl group, a 3-benzyloxyphenyl group, a fluorine atom or a hydrogen atom.

X is preferably a vinylene group (CH=CH group), an oxygen atom, a sulfur atom or a methylamino group, and more preferably a vinylene group (CH=CH group) or a methylamino group.

Y is preferably a single bond, an oxygen atom, a sulfur atom or a carbonyl group, and more preferably a single bond, an oxygen atom or a carbonyl group.

Z is preferably a single bond or a C1-C8 alkylene group, and more preferably a single bond, trimethylene, tetramethylene or octamethylene.

n is preferably 2 or 3, and more preferably 2.

Among compounds that can be used as substrates of the human FN3K and/or FN3KRP of the present invention, compounds preferred as amino alcohol derivatives represented by general formula (I) include 2-amino-2-methyl-4-[1-methyl-5-(5-phenylpentanoyl)pyrrol-2-yl]butan-1-ol,
2-amino-2-methyl-4-{1-methyl-5-[5-(2-methylphenyl)pentanoyl]pyrrol-2-yl}butan-1-ol,
2-amino-2-methyl-4-{1-methyl-5-[5-(3-methylphenyl)pentanoyl]pyrrol-2-yl}butan-1-ol,
2-amino-2-methyl-4-{1-methyl-5-[5-(4-methylphenyl)pentanoyl]pyrrol-2-yl}butan-1-ol,
2-amino-2-methyl-4-{1-methyl-5-[5-(2,3-dimethylphenyl)pentanoyl]pyrrol-2-yl}butan-1-ol,
2-amino-2-methyl-4-{1-methyl-5-[5-(2,4-dimethylphenyl)pentanoyl]pyrrol-2-yl}butan-1-ol,
2-amino-2-methyl-4-{1-methyl-5-[5-(2,5-dimethylphenyl)pentanoyl]pyrrol-2-yl}butan-1-ol,
2-amino-2-methyl-4-{1-methyl-5-[5-(3,4-dimethylphenyl)pentanoyl]pyrrol-2-yl}butan-1-ol,
2-amino-2-methyl-4-{1-methyl-5-[5-(3,5-dimethylphenyl)pentanoyl]pyrrol-2-yl}butan-1-ol,
2-amino-2-methyl-4-{1-methyl-5-[5-(3-methyl-4-methoxyphenyl)pentanoyl]pyrrol-2-yl}butan-1-ol,
2-amino-2-methyl-4-{1-methyl-5-[5-(3-methoxy-4-methylphenyl)pentanoyl]pyrrol-2-yl}butan-1-ol,
2-amino-2-methyl-4-{1-methyl-5-[5-(4-cyanophenyl)pentanoyl]pyrrol-2-yl}butan-1-ol,
2-amino-2-methyl-4-{1-methyl-5-[4-(2-methylphenyl)butanoyl]pyrrol-2-yl}butan-1-ol,
2-amino-2-methyl-4-{1-methyl-5-[4-(3-methylphenyl)butanoyl]pyrrol-2-yl}butan-1-ol,
2-amino-2-methyl-4-{1-methyl-5-[4-(4-methylphenyl)butanoyl]pyrrol-2-yl}butan-1-ol,
2-amino-2-methyl-4-{1-methyl-5-[4-(2,3-dimethylphenyl)butanoyl]pyrrol-2-yl}butan-1-ol,
2-amino-2-methyl-4-{1-methyl-5-[4-(2,4-dimethylphenyl)butanoyl]pyrrol-2-yl}butan-1-ol,
2-amino-2-methyl-4-{1-methyl-5-[4-(2,5-dimethylphenyl)butanoyl]pyrrol-2-yl}butan-1-ol,
2-amino-2-methyl-4-{1-methyl-5-[4-(3,4-dimethylphenyl)butanoyl]pyrrol-2-yl}butan-1-ol,
2-amino-2-methyl-4-{1-methyl-5-[4-(3,5-dimethylphenyl)butanoyl]pyrrol-2-yl}butan-1-ol,
2-amino-2-methyl-4-{1-methyl-5-[4-(3-methyl-4-methoxyphenyl)butanoyl]pyrrol-2-yl}butan-1-ol,
2-amino-2-methyl-4-{1-methyl-5-[4-(3-methoxy-4-methylphenyl)butanoyl]pyrrol-2-yl}butan-1-ol,
2-amino-2-methyl-4-{1-methyl-5-[4-(4-cyanophenyl)butanoyl]pyrrol-2-yl}butan-1-ol,
2-amino-2-[2-(4-octylphenyl)ethyl]propan-1,3-diol,
2-amino-2-[2-(4-heptyloxyphenyl)ethyl]propan-1,3-diol,
2-amino-2-{2-[4-(5-phenylpentanoyl)phenyl]ethyl}propan-1,3-diol,
2-amino-2-{2-[4-(5-cyclohexylpentanoyl)phenyl]ethyl}propan-1,3-diol,
2-amino-2-{2-[4-(7-phenylheptanoyl)phenyl]ethyl}propan-1,3-diol,
2-amino-2-(2-{4-[2-(4-methoxyphenyl)ethoxy]phenyl}ethyl)propan-1,3-diol,
2-amino-2-(2-{4-[2-(4-ethoxyphenyl)ethoxy]phenyl}ethyl)propan-1,3-diol,
2-amino-2-(2-{4-[2-(3-fluoro-4-methoxyphenyl)ethoxy]phenyl}ethyl)propan-1,3-diol,
2-amino-2-methyl-4-[4-(4,4,5,5,5-pentafluoropentyloxy)phenyl]butan-1-ol,
2-amino-2-methyl-4-[4-(3-biphenyl-4-ylpropoxy)phenyl]butan-1-ol,
2-amino-2-methyl-4-[4-(3-biphenyl-4-ylpropionyl)phenyl]butan-1-ol,
2-amino-2-methyl-4-[3-methoxy-4-(4-phenylbutoxy)phenyl]butan-1-ol,
2-amino-2-methyl-4-[4-(5-phenylpentyloxy)phenyl]butan-1-ol,
2-amino-2-methyl-4-[4-(5-phenylpentanoyl)phenyl]butan-1-ol,
2-amino-2-methyl-4-(4-hexyloxyphenyl)butan-1-ol,
2-amino-2-methyl-4-[4-(3-phenylpropoxy)phenyl]butan-1-ol,
2-amino-2-methyl-4-[4-(3-cyclohexylpropoxy)phenyl]butan-1-ol,
2-amino-2-methyl-4-[4-(5-cyclohexylpentanoyl)phenyl]butan-1-ol,
2-amino-2-methyl-4-(4-heptyloxyphenyl)butan-1-ol,
2-amino-2-[4-(3-benzyloxyphenoxy)-2-chlorophenyl]propyl-1,3-propanediol,
2-amino-2-[4-(3-benzyloxyphenylthio)-2-chlorophenyl]propyl-1,3-propanediol,
2-amino-2-methyl-5-[4-(3-benzyloxyphenoxy)-2-chlorophenyl]pentan-1-ol,
2-amino-2-methyl-5-[4-(3-benzyloxyphenylthio)-2-chlorophenyl]pentan-1-ol,
2-amino-2-methyl-4-[5-(5-phenylpentanoyl)thiophen-2-yl]butan-1-ol,
2-amino-2-[4-(3-benzyloxyphenylthio)-2-chlorophenyl]propyl-1,3-propanediol (ROX-2127),
2-amino-2-[4-(3-benzyloxyphenylthio)-2-chlorophenyl]ethyl-1,3-propanediol (KRP-203),
2-amino-2-methyl-4-[1-methyl-5-(5-phenylpentanoyl)pyrrol-2-yl]butan-1-ol,
2-amino-2-methyl-4-{1-methyl-5-[4-(4-methylphenyl)butanoyl]pyrrol-2-yl}butan-1-ol,
2-amino-2-methyl-4-{3-methyl-5-[4-(3,4-dimethylphenyl)butanoyl]thiophen-2-yl}butan-1-ol,
2-amino-2-methyl-4-{3-methyl-5-[4-(3,4-dimethoxyphenyl)butanoyl]thiophen-2-yl}butan-1-ol,
2-amino-2-methyl-4-{1-methyl-5-[4-(3,4-dimethylphenyl)butanoyl]pyrrol-2-yl}butan-1-ol,
2-amino-2-methyl-4-{3-chloro-5-[4-(3,4-dimethylphenyl)butanoyl]thiophen-2-yl}butan-1-ol,
2-amino-2-methyl-4-{1,3-dimethyl-5-[4-(3,4-dimethylphenyl)butanoyl]pyrrol-2-yl}butan-1-ol,
2-amino-2-methyl-4-{1-methyl-3-chloro-5-[4-(3,4-dimethoxyphenyl)butanoyl]pyrrol-2-yl}butan-1-ol,
2-amino-2-methyl-4-{1,3-dimethyl-5-[4-(3,4-dimethoxyphenyl)butanoyl]pyrrol-2-yl}butan-1-ol,
2-amino-2-methyl-3-(4-heptanoylphenoxy)propan-1-ol, 2-amino-2-methyl-5-{1-methyl-5-[4-(4-methylphenyl)butanoyl]pyrrol-2-yl}pentan-1-ol,
2-amino-2-methyl-5-{5-[4-(4-methylphenyl)butanoyl]thiophen-2-yl}pentan-1-ol,
2-amino-2-methyl-3-{4-[4-(4-methylphenyl)butanoyl]phenylmethoxy}propan-1-ol,
2-amino-2-methyl-3-{2-chloro-4-[4-(4-methylphenyl)butanoyl]phenylmethoxy}propan -1-ol,
2-amino-2-methyl-3-{5-[4-(3,4-dimethylphenyl)butanoyl]thiophen-2-ylmethoxy}propan -1-ol, and
2-amino-2-[2-(4-octylphenyl)ethyl]propan-1,3-diol (FTY720).

More preferred compounds include (2R)-2-amino-2-methyl-4-[1-methyl-5-(5-phenylpentanoyl)pyrrol-2-yl]butan-1-ol,
(2R)-2-amino-2-methyl-4-{1-methyl-5-[5-(2-methylphenyl)pentanoyl]pyrrol-2-yl}butan -1-ol,
(2R)-2-amino-2-methyl-4-{1-methyl-5-[5-(3-methylphenyl)pentanoyl]pyrrol-2-yl}butan -1-ol,
(2R)-2-amino-2-methyl-4-{1-methyl-5-[5-(4-methylphenyl)pentanoyl]pyrrol-2-yl}butan -1-ol,
(2R)-2-amino-2-methyl-4-{1-methyl-5-[5-(2,3-dimethylphenyl)pentanoyl]pyrrol-2-yl}butan-1-ol,
(2R)-2-amino-2-methyl-4-{1-methyl-5-[5-(2,4-dimethylphenyl)pentanoyl]pyrrol-2-yl}butan-1-ol,
(2R)-2-amino-2-methyl-4-{1-methyl-5-[5-(2,5-dimethylphenyl)pentanoyl]pyrrol-2-yl}butan-1-ol,
(2R)-2-amino-2-methyl-4-{1-methyl-5-[5-(3,4-dimethylphenyl)pentanoyl]pyrrol-2-yl}butan-1-ol,
(2R)-2-amino-2-methyl-4-{1-methyl-5-[5-(3,5-dimethylphenyl)pentanoyl]pyrrol-2-yl}butan-1-ol,
(2R)-2-amino-2-methyl-4-{1-methyl-5-[5-(3-methyl-4-methoxyphenyl)pentanoyl]pyrrol -2-yl}butan-1-ol,
(2R)-2-amino-2-methyl-4-{1-methyl-5-[5-(3-methoxy-4-methylphenyl)pentanoyl]pyrrol -2-yl}butan-1-ol,
(2R)-2-amino-2-methyl-4-{1-methyl-5-[5-(4-cyanophenyl)pentanoyl]pyrrol-2-yl}butan -1-ol,
(2R)-2-amino-2-methyl-4-{1-methyl-5-[4-(2-methylphenyl)butanoyl]pyrrol-2-yl}butan -1-ol,
(2R)-2-amino-2-methyl-4-{1-methyl-5-[4-(3-methylphenyl)butanoyl]pyrrol-2-yl}butan -1-ol,
(2R)-2-amino-2-methyl-4-{1-methyl-5-[4-(4-methylphenyl)butanoyl]pyrrol-2-yl}butan -1-ol,
(2R)-2-amino-2-methyl-4-{1-methyl-5-[4-(2,3-dimethylphenyl)butanoyl]pyrrol-2-yl}butan-1-ol,
(2R)-2-amino-2-methyl-4-{1-methyl-5-[4-(2,4-dimethylphenyl)butanoyl]pyrrol-2-yl}butan-1-ol,
(2R)-2-amino-2-methyl-4-{1-methyl-5-[4-(2,5-dimethylphenyl)butanoyl]pyrrol-2-yl}butan-1-ol,
(2R)-2-amino-2-methyl-4-{1-methyl-5-[4-(3,4-dimethylphenyl)butanoyl]pyrrol-2-yl}butan-1-ol,
(2R)-2-amino-2-methyl-4-{1-methyl-5-[4-(3,5-dimethylphenyl)butanoyl]pyrrol-2-yl}butan-1-ol,
(2R)-2-amino-2-methyl-4-{1-methyl-5-[4-(3-methyl-4-methoxyphenyl)butanoyl]pyrrol -2-yl}butan-1-ol,
(2R)-2-amino-2-methyl-4-{1-methyl-5-[4-(3-methoxy-4-methylphenyl)butanoyl]pyrrol -2-yl}butan-1-ol
(2R)-2-amino-2-methyl-4-{1-methyl-5-[4-(4-cyanophenyl)butanoyl]pyrrol-2-yl}butan-1-ol,
(2R)-2-amino-2-[2-(4-octylphenyl)ethyl]propan-1,3-diol,
(2R)-2-amino-2-[2-(4-heptyloxyphenyl)ethyl]propan-1,3-diol,
(2R)-2-amino-2-{2-[4-(5-phenylpentanoyl)phenyl]ethyl}propan-1,3-diol,
(2R)-2-amino-2-{2-[4-(5-cyclohexylpentanoyl)phenyl]ethyl}propan-1,3-diol,
(2R)-2-amino-2-{2-[4-(7-phenylheptanoyl)phenyl]ethyl}propan-1,3-diol,
(2R)-2-amino-2-(2-{4-[2-(4-methoxyphenyl)ethoxy]phenyl}ethyl)propan-1,3-diol,
(2R)-2-amino-2-(2-{4-[2-(4-ethoxyphenyl)ethoxy]phenyl}ethyl)propan-1,3-diol,
(2R)-2-amino-2-(2-{4-[2-(3-fluoro-4-methoxyphenyl)ethoxy]phenyl}ethyl)propan-1,3-diol,
(2R)-2-amino-2-methyl-4-[4-(4,4,5,5,5-pentafluoropentyloxy)phenyl]butan-1-ol,
(2R)-2-amino-2-methyl-4-[4-(3-biphenyl-4-ylpropoxy)phenyl]butan-1-ol,
(2R)-2-amino-2-methyl-4-[4-(3-biphenyl-4-ylpropionyl)phenyl]butan-1-ol,
(2R)-2-amino-2-methyl-4-[3-methoxy-4-(4-phenylbutoxy)phenyl]butan-1-ol,
(2R)-2-amino-2-methyl-4-[4-(5-phenylpentyloxy)phenyl]butan-1-ol,
(2R)-2-amino-2-methyl-4-[4-(5-phenylpentanoyl)phenyl]butan-1-ol,
(2R)-2-amino-2-methyl-4-(4-hexyloxyphenyl)butan-1-ol,
(2R)-2-amino-2-methyl-4-[4-(3-phenylpropoxy)phenyl]butan-1-ol,
(2R)-2-amino-2-methyl-4-[4-(3-cyclohexylpropoxy)phenyl]butan-1-ol,
(2R)-2-amino-2-methyl-4-[4-(5-cyclohexylpentanoyl)phenyl]butan-1-ol,
(2R)-2-amino-2-methyl-4-(4-heptyloxyphenyl)butan-1-ol,
(2R)-2-amino-2-methyl-2-[4-(3-benzyloxyphenoxy)-2-chlorophenyl]propyl-1,3 -propanediol,
(2R)-2-amino-2-[4-(3-benzyloxyphenylthio)-2-chlorophenyl]propyl-1,3-propanediol,
(2R)-2-amino-2-methyl-5-[4-(3-benzyloxyphenoxy)-2-chlorophenyl]pentan-1-ol,
(2R)-2-amino-2-methyl-5-[4-(3-benzyloxyphenylthio)-2-chlorophenyl]pentan-1-ol,
(2R)-2-amino-2-methyl-4-[5-(5-phenylpentanoyl)thiophen-2-yl]butan-1-ol,
(2R)-2-amino-2-[4-(3-benzyloxyphenylthio)-2-chlorophenyl]propyl-1,3-propanediol (ROX-2127),
(2R)-2-amino-2-[4-(3-benzyloxyphenylthio)-2-chlorophenyl]ethyl-1,3-propanediol (KRP-203),
(2R)-2-amino-2-methyl-4-[1-methyl-5-(5-phenylpentanoyl)pyrrol-2-yl]butan-1-ol,
(2R)-2-amino-2-methyl-4-{1-methyl-5-[4-(4-methylphenyl)butanoyl]pyrrol-2-yl}butan -1-ol,
(2R)-2-amino-2-methyl-4-{3-methyl-5-[4-(3,4-dimethylphenyl)butanoyl]thiophen-2-yl}butan-1-ol,
(2R)-2-amino-2-methyl-4-{3-methyl-5-[4-(3,4-dimethoxyphenyl)butanoyl]thiophen-2-yl}butan-1-ol,
(2R)-2-amino-2-methyl-4-{1-methyl-5-[4-(3,4-dimethylphenyl)butanoyl]pyrrol-2-yl}butan-1-ol,
(2R)-2-amino-2-methyl-4-{3-chloro-5-[4-(3,4-dimethylphenyl)butanoyl]thiophen-2-yl}butan-1-ol,
(2R)-2-amino-2-methyl-4-{1,3-dimethyl-5-[4-(3,4-dimethylphenyl)butanoyl]pyrrol-2-yl}butan-1-ol,
(2R)-2-amino-2-methyl-4-{1-methyl-3-chloro-5-[4-(3,4-dimethoxyphenyl)butanoyl]pyrrol-2-yl}butan-1-ol,
(2R)-2-amino-2-methyl-4-{1,3-dimethyl-5-[4-(3,4-dimethoxyphenyl)butanoyl]pyrrol-2-yl}butan-1-ol,
(2S)-2-amino-2-methyl-3-(4-heptanoylphenoxy)propan-1-ol,
(2R)-2-amino-2-methyl-5-{1-methyl-5-[4-(4-methylphenyl)butanoyl]pyrrol-2-yl}pentan -1-ol,
(2R)-2-amino-2-methyl-5-{5-[4-(4-methylphenyl)butanoyl]thiophen-2-yl}pentan-1-ol, (2S)-2-amino-2-methyl-3-{4-[4-(4-methylphenyl)butanoyl]phenylmethoxy}pentan-1-ol,
(2S)-2-amino-2-methyl-3-{2-chloro-4-[4-(4-methylphenyl)butanoyl]phenylmethoxy}propan-1-ol,
(2S)-2-amino-2-methyl-3-{5-[4-(3,4-dimethylphenyl)butanoyl]thiophen-2-ylmethoxy}pentan-1-ol, and
(2R)-2-amino-2-[2-(4-octylphenyl)ethyl]propan-1,3-diol (FTY720).

Particularly preferred compounds include (2R)-2-amino-2-methyl-4-[1-methyl-5-(5-phenylpentanoyl)pyrrol-2-yl]butan-1-ol,
(2R)-2-amino-2-methyl-4-{1-methyl-5-[5-(4-methylphenyl)pentanoyl]pyrrol-2-yl}butan-1-ol,
(2R)-2-amino-2-methyl-4-{1-methyl-5-[5-(3,4-dimethylphenyl)pentanoyl]pyrrol-2-yl}butan-1-ol,
(2R)-2-amino-2-methyl-4-{1-methyl-5-[5-(3-methyl-4-methoxyphenyl)pentanoyl]pyrrol-2-yl}butan-1-ol,
(2R)-2-amino-2-methyl-4-{1-methyl-5-[5-(3-methoxy-4-methylphenyl)pentanoyl]pyrrol-2-yl}butan-1-ol,
(2R)-2-amino-2-methyl-4-{1-methyl-5-[5-(4-cyanophenyl)pentanoyl]pyrrol-2-yl}butan-1-ol,
(2R)-2-amino-2-methyl-4-{1-methyl-5-[4-(4-methylphenyl)butanoyl]pyrrol-2-yl}butan-1-ol,
(2R)-2-amino-2-methyl-4-{1-methyl-5-[4-(3,4-dimethylphenyl)butanoyl]pyrrol-2-yl}butan-1-ol,
(2R)-2-amino-2-methyl-4-{1-methyl-5-[4-(3-methyl-4-methoxyphenyl)butanoyl]pyrrol-2-yl}butan-1-ol,
(2R)-2-amino-2-methyl-4-{1-methyl-5-[4-(3-methoxy-4-methylphenyl)butanoyl]pyrrol-2-yl}butan-1-ol,
(2R)-2-amino-2-methyl-4-{1-methyl-5-[4-(4-cyanophenyl)butanoyl]pyrrol-2-yl}butan-1-ol,
(2R)-2-amino-2-[2-(4-octylphenyl)ethyl]propan-1,3-diol.

More particularly preferred compounds include (2R)-2-amino-2-methyl-4-[1-methyl-5-(5-phenylpentanoyl)pyrrol-2-yl]butan-1-ol,
(2R)-2-amino-2-methyl-4-{1-methyl-5-[4-(4-methylphenyl)butanoyl]pyrrol-2-yl}butan-1-ol,
(2R)-2-amino-2-methyl-4-{1-methyl-5-[4-(3,4-dimethylphenyl)butanoyl]pyrrol-2-yl}butan-1-ol,
(2R)-2-amino-2-methyl-4-{1-methyl-5-[4-(3-methyl-4-methoxyphenyl)butanoyl]pyrrol-2-yl}butan-1-ol,
(2R)-2-amino-2-methyl-4-{1-methyl-5-[4-(3-methoxy-4-methylphenyl)butanoyl]pyrrol-2-yl}butan-1-ol,
(2R)-2-amino-2-methyl-4-{1-methyl-5-[4-(4-cyanophenyl)butanoyl]pyrrol-2-yl}butan-1-ol, and
(2R)-2-amino-2-[2-(4-octylphenyl)ethyl]propan-1,3-diol.

The structural formulae of compounds preferred as amino alcohol derivatives represented by general formula (I) will be shown below.

| Compound No. | Structural formula |
| --- | --- |
| 1 | |
| 2 | |
| 3 | |
| 4 | |
| 5 | |

-continued
| Compound No. | Structural formula |
|---|---|
| 6 | 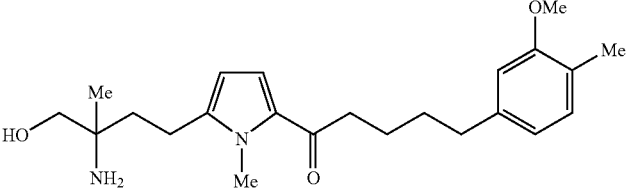 |
| 7 | 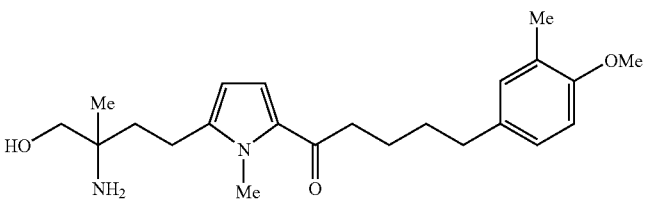 |
| 8 | 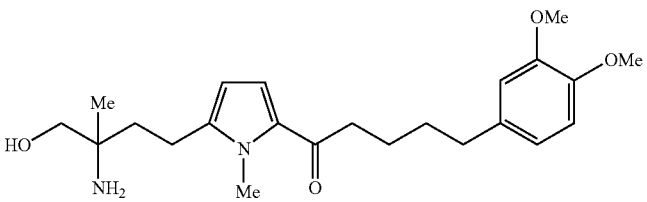 |
| 9 | 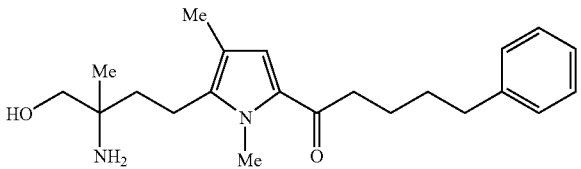 |
| 10 | 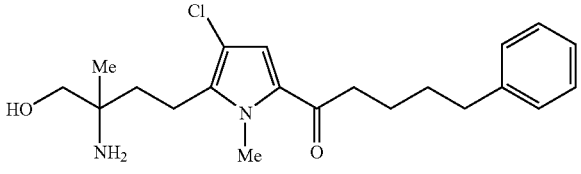 |
| 11 | 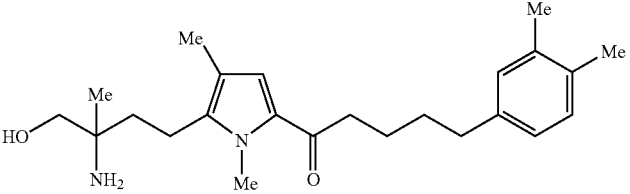 |
| 12 | 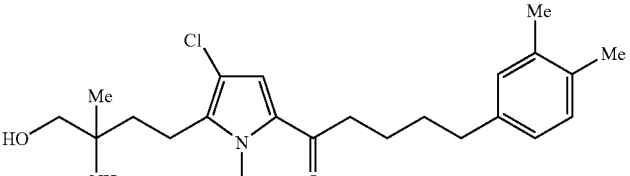 |

-continued

| Compound No. | Structural formula |
|---|---|
| 13 | |
| 14 | |
| 15 | |
| 16 | |
| 17 | |
| 18 | |
| 19 | |
| 20 | |
| 21 | |

-continued
| Compound No. | Structural formula |
|---|---|
| 22 | 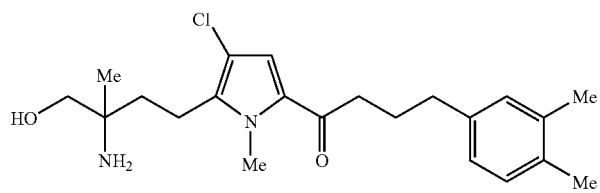 |
| 23 | 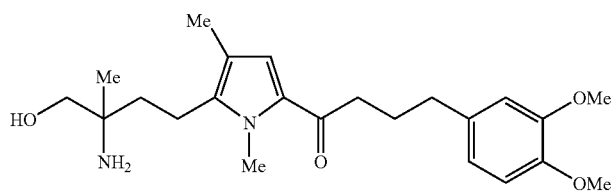 |
| 24 | 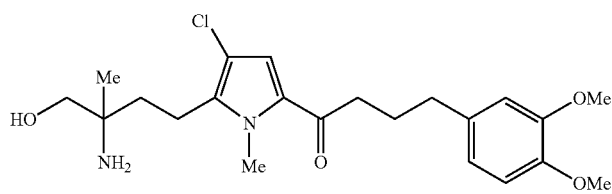 |
| 25 | 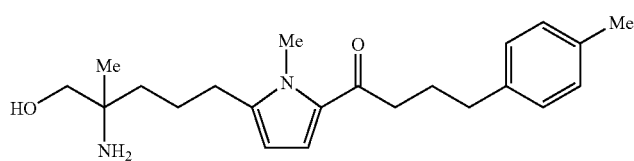 |
| 26 | 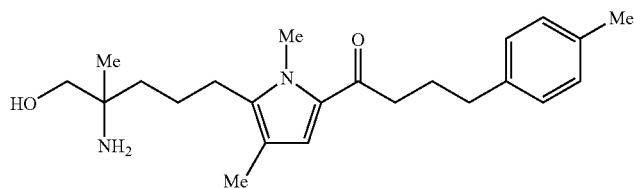 |
| 27 | 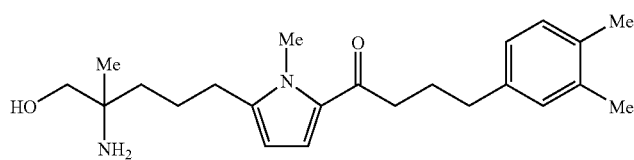 |
| 28 | 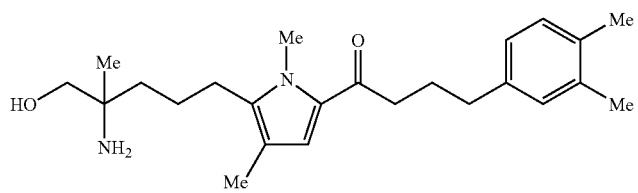 |
| 29 | 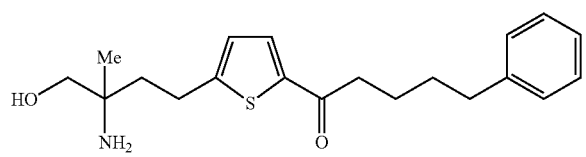 |

| Compound No. | Structural formula |
|---|---|
| 30 | 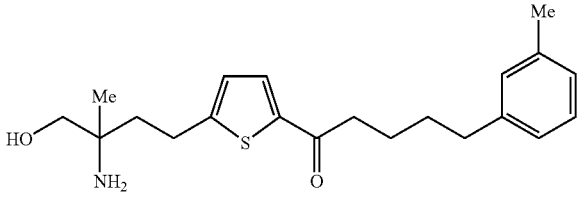 |
| 31 | 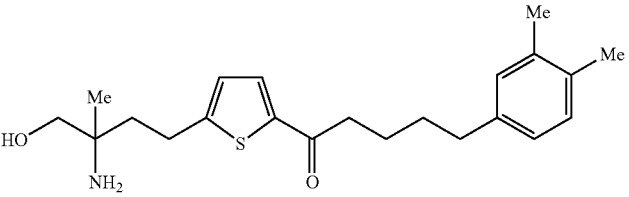 |
| 32 | 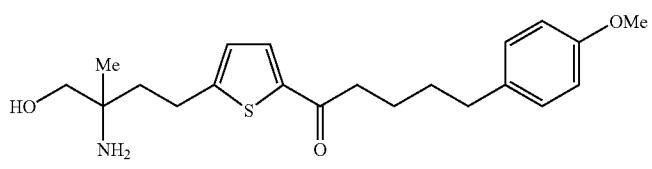 |
| 33 | 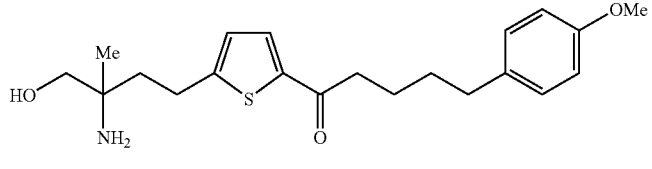 |
| 34 | 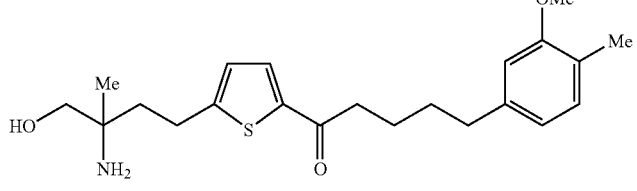 |
| 35 | 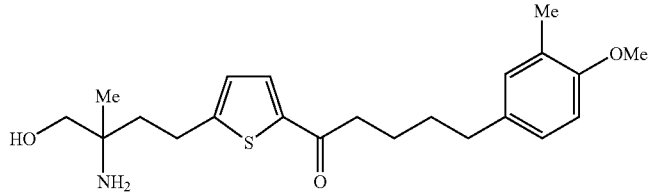 |
| 36 | 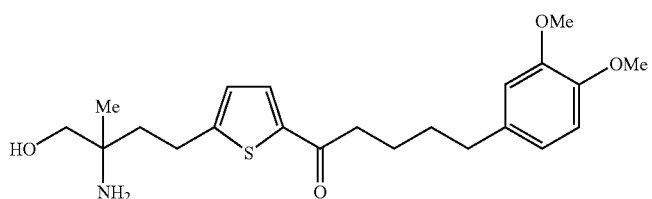 |
| 37 | 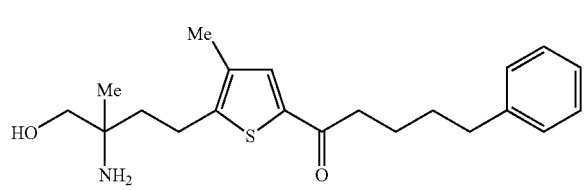 |

-continued
| Compound No. | Structural formula |
|---|---|
| 38 | 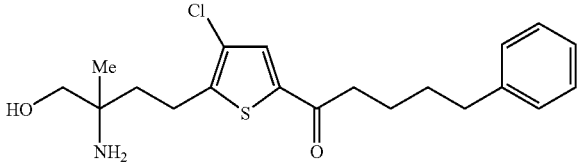 |
| 39 | 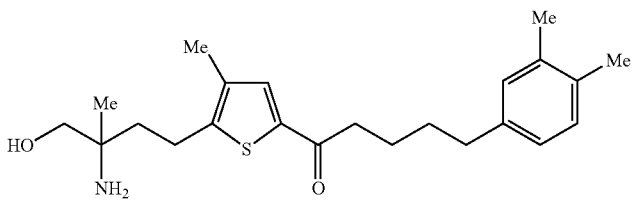 |
| 40 | 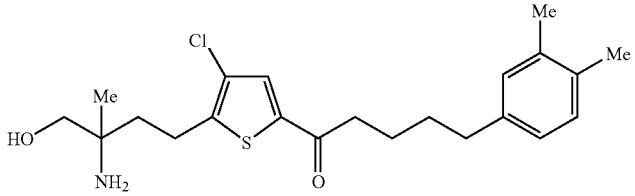 |
| 41 | 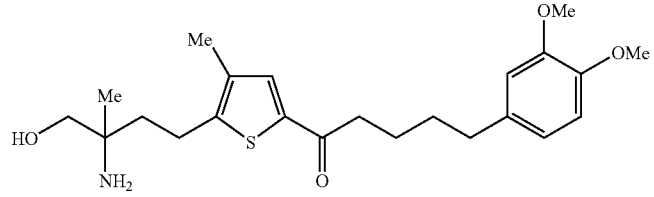 |
| 42 | 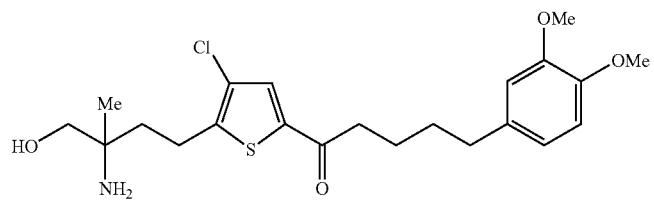 |
| 43 | 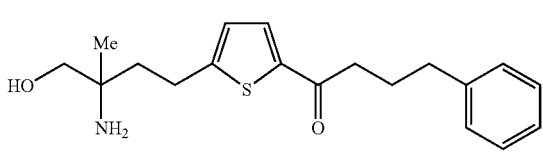 |
| 44 | 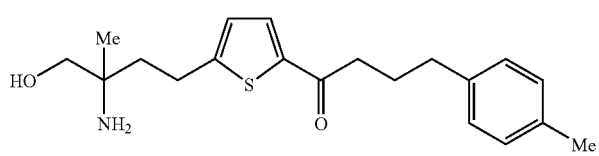 |
| 45 | 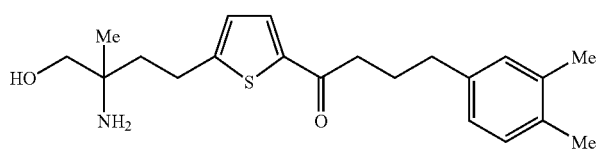 |

-continued

| Compound No. | Structural formula |
| --- | --- |
| 46 | (structure: HO-CH2-C(Me)(NH2)-CH2CH2-[thiophene]-C(=O)-CH2CH2CH2-[3,4-dimethoxyphenyl]) |
| 47 | (structure: HO-CH2-C(Me)(NH2)-CH2CH2-[4-methylthiophene]-C(=O)-CH2CH2CH2-[3,4-dimethylphenyl]) |
| 48 | (structure: HO-CH2-C(Me)(NH2)-CH2CH2-[4-chlorothiophene]-C(=O)-CH2CH2CH2-[3,4-dimethylphenyl]) |
| 49 | (structure: HO-CH2-C(Me)(NH2)-CH2CH2-[4-methylthiophene]-C(=O)-CH2CH2CH2-[3,4-dimethoxyphenyl]) |
| 50 | (structure: HO-CH2-C(Me)(NH2)-CH2CH2-[4-chlorothiophene]-C(=O)-CH2CH2CH2-[3,4-dimethoxyphenyl]) |
| 51 | (structure: HO-CH2-C(Me)(NH2)-CH2CH2CH2-[3-methylthiophene]-C(=O)-CH2CH2CH2-[4-methylphenyl]) |
| 52 | (structure: HO-CH2-C(Me)(NH2)-CH2CH2CH2-[3-methylthiophene]-C(=O)-CH2CH2CH2-[4-methylphenyl]) |
| 53 | (structure: HO-CH2-C(Me)(NH2)-CH2CH2CH2-[thiophene]-C(=O)-CH2CH2CH2-[3,4-dimethylphenyl]) |

-continued
| Compound No. | Structural formula |
|---|---|
| 54 | 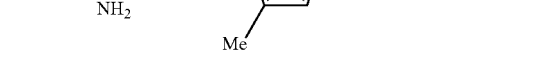 |
| 55 |  |
| 56 | 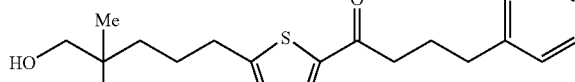 |
| 57 | 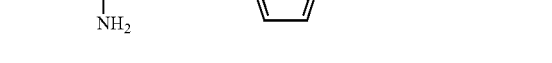 |
| 58 |  |
| 59 | 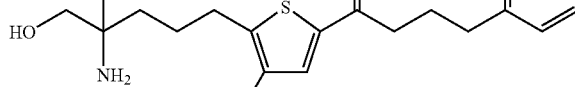 |
| 60 |  |
| 61 | 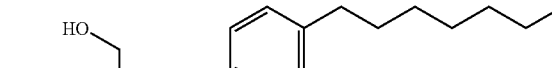 |
| 62 | 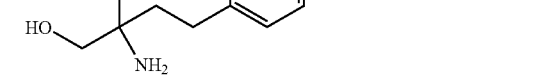 |

-continued
| Compound No. | Structural formula |
|---|---|
| 63 | 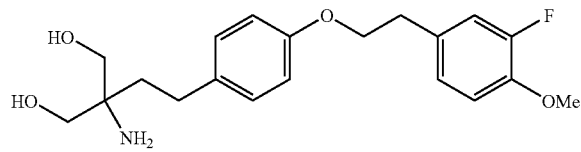 |
| 64 | 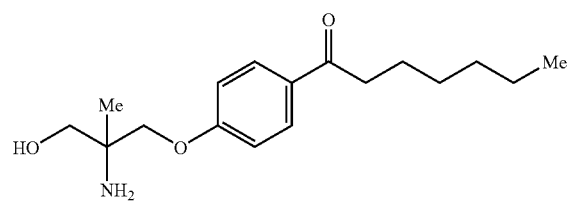 |
| 65 | 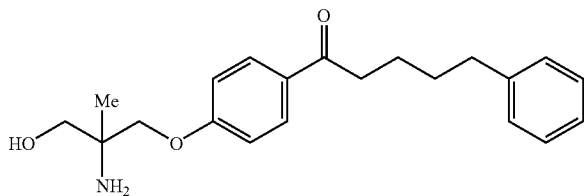 |
| 66 | 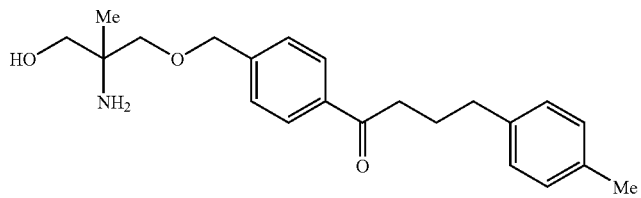 |
| 67 | 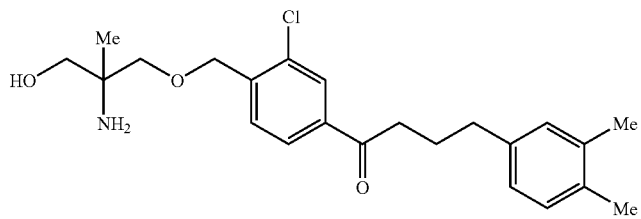 |
| 68 | 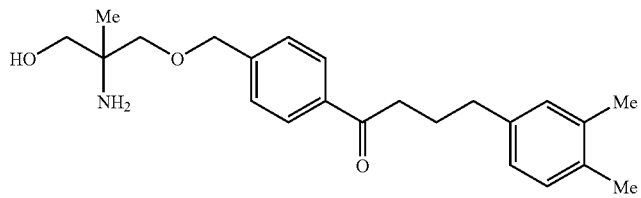 |
| 69 | 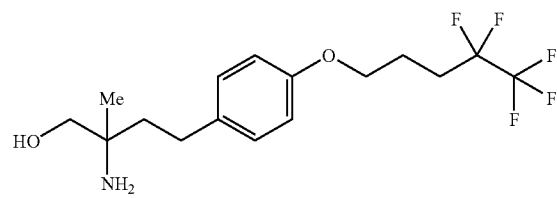 |

-continued
| Compound No. | Structural formula |
|---|---|
| 70 | 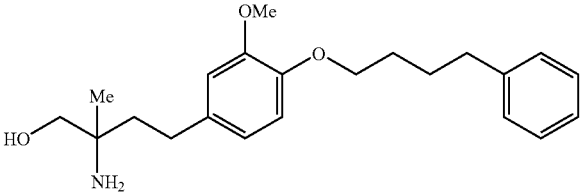 |
| 71 | 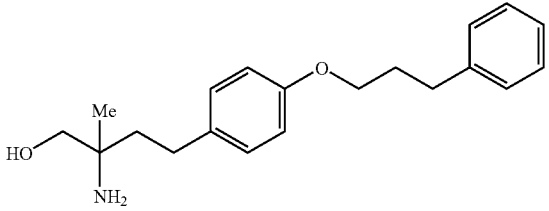 |
| 72 | 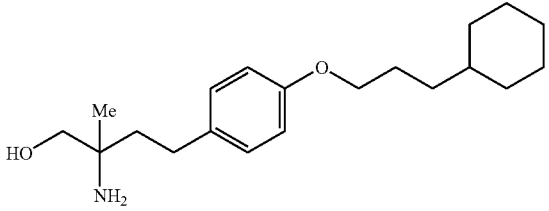 |
| 73 | 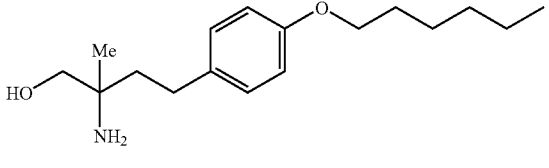 |
| 74 | 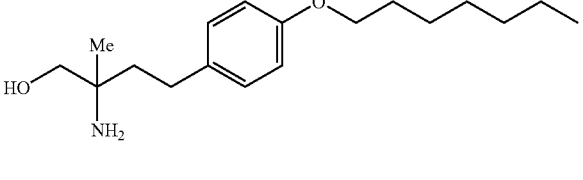 |
| 75 | 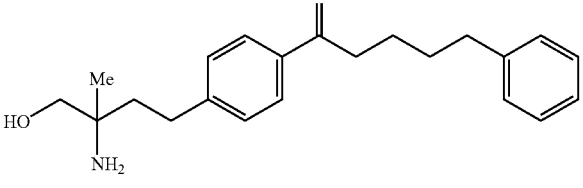 |
| 76 | 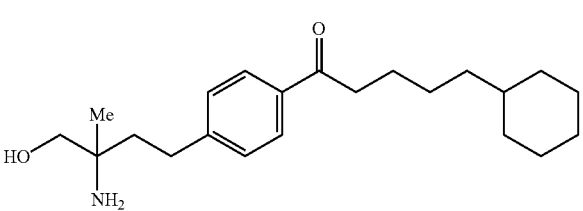 |

-continued

| Compound No. | Structural formula |
|---|---|
| 77 | |
| 78 | |
| 79 | |
| 80 | |
| 81 | |
| 82 | |

Examples of the "C1-C6 alkyl group" in the definitions of the aforementioned $R^1$, $R^2$, $R^3$, $R^4$ and $R^5$ include a methyl group, an ethyl group, a propyl group, an isopropyl group, a butyl group, a 2-methylpropyl group, a 3-methylpropyl group, a 2,2,2-trimethylmethyl group, a pentyl group, and a hexyl group. Preferred examples of the "C1-C6 alkyl group" include a methyl group, an ethyl group, and a propyl group. More preferred examples include a methyl group and an ethyl group.

The "halogen atom" in the definitions of the aforementioned $R^4$ and $R^5$ is a fluorine atom, a chlorine atom, a bromine atom, or an iodine atom. The "halogen atom" is preferably a fluorine atom or a chlorine atom.

Examples of the "C1-C6 alkoxy group" in the definitions of the aforementioned $R^4$ and $R^5$ include a methoxy group, an ethoxy group, a propoxy group, an isopropoxy group, a butoxy group, a 2-methylpropoxy group, a 3-methylpropoxy group, a 2,2,2-trimethylmethoxy group, a pentyloxy group, and a hexyloxy group. Preferred examples of the "C1-C6 alkoxy group" include a methoxy group and an ethoxy group.

Examples of the "C3-C6 cycloalkyl group" in the definitions of the aforementioned $R^5$ include a cyclopropyl group, a cyclobutyl group, a cyclopentyl group, and a cyclohexyl group. Preferred examples of the "C3-C6 cycloalkyl group" include a cyclopropyl group and a cyclohexyl group.

Examples of the "halogeno C1-C6 alkyl group" in the definitions of the aforementioned $R^5$ include groups formed by substituting the aforementioned C1-C6 alkyl groups with halogen atoms, such as a fluoromethyl group, a difluoromethyl group, a trifluoromethyl group, a fluoroethyl group, a difluoroethyl group, a trifluoroethyl group, a fluoropropyl group, a difluoropropyl group, a trifluoropropyl group, a fluorobutyl group, a difluorobutyl group, a trifluorobutyl group, a fluoropentyl group, a difluoropentyl group, a trifluoropentyl group, a fluorohexyl group, a difluorohexyl group, a trifluorohexyl group, a pentafluoroethyl group, a hexafluoropropyl group, a nonafluorobutyl group, a chloromethyl group, a dichloromethyl group, a trichloromethyl group, a chloroethyl group, a dichloroethyl group, a trichloroethyl group, chloropropyl group, dichloropropyl group, a trichloropropyl group, a chlorobutyl group, a dichlorobutyl group, a trichlorobutyl group, a chloropentyl group, a dichloropentyl group, a trichloropentyl group, a chlorohexyl group, a dichlorohexyl group, a trichlorohexyl group, a pentachloroethyl group, a hexachloropropyl group, and a nonachlorobutyl group. Preferred examples of the "halogeno C1-C6 alkyl group" include a fluoromethyl group, a difluoromethyl group, a trifluoromethyl group, a fluoroethyl group, a difluoroethyl group, a trifluoroethyl group, a fluoropropyl group, a difluoropropyl group, and a trifluoropropyl group. More preferred examples of the "halogeno C1-C6 alkyl group" include a trifluoromethyl group and a trifluoroethyl group.

Examples of the "C1-C8 alkylene group" in the definitions of the aforementioned Z include a methylene group, an ethylene group, a propylene group, a tetramethylene group, a pentamethylene group, a hexamethylene group, a heptamethylene group, and an octamethylene group. A preferred example of the "C1-C8 alkylene group" is an alkylene group having 2 to 8 carbon atoms. More preferred examples include an ethylene group, a propylene group, a tetramethylene group, a heptamethylene group, and an octamethylene group.

Examples of the "C1-C8 alkylene group substituted with 2 to 8 fluorine atoms" in the definitions of the aforementioned Z include a difluoromethylene group, a 1,1-difluoroethylene group, a 1,1,2,2-tetrafluoroethylene group, a 1,1-difluoropropylene group, a 1,1,2,2-tetrafluoropropylene group, a 1,1-difluorotetramethylene group, a 1,1,2,2-tetrafluorotetramethylene group, a 1,1-difluoropentamethylene group, and a 1,1,2,2-tetrafluoropentamethylene group. Preferred examples of the "C1-C8 alkylene group substituted with 2 to 8 fluorine atoms" include a 1,1-difluoropropylene group, a 1,1,2,2-tetrafluoropropylene group, a 1,1-difluorotetramethylene group, a 1,1,2,2-tetrafluorotetramethylene group, a 1,1-difluoropentamethylene group, and a 1,1,2,2-tetrafluoropentamethylene group.

The amino alcohol derivative represented by the above general formula (I) has an amino group as a basic group. Thus, the aforementioned "salt" means a salt obtained as a result of the reaction of the amino alcohol derivative with an acid. Examples of such a salt include: inorganic acid salts including halogen acid salts such as a hydrofluoric acid salt, hydrochloride, hydrobromide or hydroiodide, nitrate, perchlorate, sulfate, and phosphate; organic acid salts including lower alkanesulfonates such as methanesulfonate, trifluoromethanesulfonate or ethanesulfonate, arylsulfonates such as benzenesulfonate or p-toluenesulfonate, acetate, malate, fumarate, succinate, citrate, ascorbate, tartrate, oxalate, and maleate; and amino acid salts such as a glycine salt, a lysine salt, an arginine salt, an ornithine salt, glutamate, and aspartate. Among these salts, hydrochloride, acetate, fumarate, succinate, and maleate are preferable.

In the present invention, when the amino alcohol derivative represented by the above general formula (I) or a pharmaceutically acceptable salt thereof has an asymmetric carbon atom in its molecule, it includes an optical isomer. Among amino alcohol derivatives represented by the above general formula (I), compounds having an asymmetric carbon atom can be represented as a single formula, namely, as the R-form. However, depending on the production method and the like, there may be cases where the S-form is mixed as a by-product. Accordingly, in such a case, the amino alcohol derivative represented by the above general formula (I) mainly includes the R-form as an optical isomer, but it partially includes the S-form as well.

When the amino alcohol derivative represented by the above general formula (I) or a pharmaceutically acceptable salt thereof is left in the air or is recrystallized, it absorbs water, and thus it contains adsorption water or becomes a hydrate. Such hydrates are also included in the pharmaceutically acceptable salt of the amino alcohol derivative represented by the above general formula (I).

6. Method of Producing Phosphoric Ester of Compound (I) Using Human FN3KRP and/or Human FN3K A compound represented by the following general formula (II) can be produced from the compound represented by the above general formula (I) using human FN3KRP and/or human FN3K:

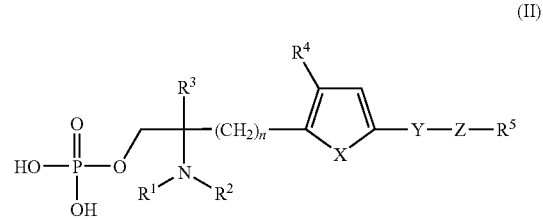

(II)

wherein $R^1$, $R^2$, $R^3$, $R^{4}$, $R^5$, X, Y and Z have the same definitions as those described for the aforementioned compound (I). Hereinafter, the compound represented by general formula (II) is also referred to as "compound (II)."

The compound (II) that is a phosphoric ester of the compound (I) can be produced by contacting the compound (I) with human FN3KRP and/or human FN3K.

A specific example of a method of producing the compound (II) is the following method. However, examples are not limited thereto, as long as it is a method capable of producing the compound (II).

(1) Human FN3KRP and/or Human FN3K

Human FN3KRP and/or human FN3K used in the production of the compound (II) can be obtained from erythrocytes according to the method described in the section 4 above, or can also be obtained from cells that express such human FN3KRP and/or human FN3K. Human FN3K and/or human FN3KRP can be used after purification. Alternatively, roughly purified products or the cell extract itself can also be used. Also, cells that express human FN3KRP and/or human FN3K can be directly used.

(2) Enzyme Reaction

The production method of the present invention can be carried out in various embodiments. Examples of the production method include: (a) a method of contacting the compound (I) with cells that express human FN3K and/or human FN3KRP; (b) a method of contacting the compound (I) with an extract from cells that express human FN3K and/or human FN3KRP; and (c) a method of contacting the compound (I) with purified or roughly purified human FN3K and/or human FN3KRP.

When the compound (II) is produced from the compound (I) using human FN3K and/or human FN3KRP, it is desired to use conditions in which the enzyme reaction occurs.

The product generated by the enzyme reaction can be analyzed by measuring the amount of the compound (II) generated as an enzyme reaction product after completion of the enzyme reaction. The amount of the compound (II) generated is not particularly limited, as long as it is sufficient for measuring the generation level of the compound (II). For example, the reaction product is subjected to HPLC to measure the peak of the compound (II), so as to carry out the measurement.

Moreover, the compound (II) as an enzyme reaction product can be purified from the reaction system.

7. Method of Screening for Substance Phosphorylated by Human FN3KRP and/or Human FN3K A substance phosphorylated by human FN3KRP and/or human FN3K can be identified by the following method. The present method comprises the following steps:

(1)
(i) contacting human FN3KRP or human FN3K with a test substance;
(ii) measuring the amount of phosphoric ester of the test substance generated; and
(iii) comparing the amount of the generated phosphoric ester measured in (ii) above with the amount of the phosphoric ester of the test substance measured when the test substance is not contacted with human FN3KRP or human FN3K, (2)
(i) contacting human FN3KRP or human FN3K with a test substance;
(ii) measuring the amount of phosphoric ester of the test substance generated;
(iii) comparing the amount of the generated phosphoric ester measured in (ii) above with the amount of the phosphoric ester of the test substance measured when the test substance is not contacted with human FN3KRP or human FN3K, and
(iv) determining that the test substance has been phosphorylated, when the amount of the phosphoric ester measured in (ii) above is greater compared with the amount of the phosphoric ester of the test substance measured when the test substance is not contacted with human FN3KRP or human FN3K.

Each step will be described below.

Concerning (1)

Regarding (1)-(i)

The type of human FN3KRP or human FN3K used in the present step is not particularly limited. Cells that express human FN3KRP or human FN3K can be directly used. Moreover, a solution of disintegrated cells, human FN3KRP or human FN3K roughly purified from such cells, and purified human FN3KRP or human FN3K can also be used. Furthermore, those obtained by the method described in the aforementioned section "4. Expression of human FN3K and/or human FN3KRP" can also be used.

As a test substance, the substances described in the aforementioned section "5. Compound phosphorylated by phosphorylating enzyme" can be used, and other compounds can also be used. Examples of such other compounds include compounds other than the compound represented by general formula (I), microbial metabolites, extracts from plant or animal tissues, derivatives thereof, and mixtures thereof. The dose and concentration of the test substance may be determined, as appropriate, or multiple types of doses may also be determined by preparing dilution series, for example. The test substance may be administered in an appropriate state such as a solid or a liquid. The test substance may also be dissolved in a suitable buffer, or a stabilizer and the like may be added to the test substance. In the case of a screening method using cultured cells, the test substance may be added to a culture medium and may then be cultured. In the case of adding the test substance to such a medium, the test substance may be added from the beginning of the culture or during the culture. Moreover, the number of additions of the test substance is not limited to once. The culture period for culturing cells in the presence of the test substance may be determined, as appropriate. It is preferably for 30 minutes to 48 hours. When the test substance is administered to an individual mammal, administration forms such as oral administration, intravenous injection, intraperitoneal injection, percutaneous injection and hypodermic injection can be used as appropriate, depending on the physical properties of the test substance, etc. Moreover, the time required from administration of the test substance to the obtainment of a sample can be selected, as appropriate.

A buffer for adjusting pH may be added to the reaction solution, as necessary.

These materials are mixed, and the following reaction is then carried out, for example.

Temperature condition: 0° C. to 45° C., preferably 37° C.
pH of the reaction solution: pH 6-9, preferably pH 7.4
Reaction time: 30 seconds to 24 hours, preferably 3 hours
The reaction can be carried out using a 384-well assay plate, for example.

Regarding (1)-(ii)

An example of a method of measuring the phosphoric ester of the test compound is a method of performing separated determination on a product using HPLC. As such a method, the following method is applied, for example. However, examples of the method are not limited thereto.

Column: YMC-Pack ODS-AA-312 (6.0 mm (diameter)×150 mm (length); particle size: 5 µm; YMC)
Mobile phase: 40% acetonitrile/0.1% trifluoroacetic acid
Flow rate: 1 mL/min
Elution method: Isocratic elution
Column temperature: 40° C.
Detection wavelength: 295 nm Regarding (1)-(iii)

The amount of the phosphoric ester of the test substance measured when the test substance is not contacted with human FN3KRP or human FN3K can be measured by the same method as that described in (1)-(ii) above. Then, the amount of the phosphoric ester of the test substance that is contacted with human FN3KRP or human FN3K can be compared with the amount of the phosphoric ester of the test substance that is not contacted with human FN3KRP or human FN3K.

Concerning (2)

Regarding (2)-(i) to (iii)

These steps can be carried out by the same methods as those described in (1)-(i) to (iii) above.

Regarding (2)-(iv)

As a result of the comparison in (2)-(iii) above, when the amount of the phosphoric ester of the test substance in (ii) above is greater than that in (iii) above, it can be determined that the test substance has been phosphorylated.

8. Method of Examining Ability of Patient to Metabolize Drug Using Phosphorylating Ability Human FN3KRP and/or human FN3K have the function of phosphorylating in vivo the compound represented by general formula (I) so as to convert it to the phosphoric ester represented by general formula (II).

According to the following method, the ability of a patient to metabolize a drug represented by general formula (I) can be examined.

(1) Method Using Expression Level of Human FN3KRP and/or Human FN3K gene as Indicator This method comprises the following steps (i) to (iii):
(i) extracting total RNA from a sample collected from a subject;
(ii) measuring the expression level of a human FN3KRP and/or human FN3K gene in the total RNA; and
(iii) comparing the expression level of the human FN3KRP and/or human FN3K gene measured in (ii) above with the expression level of the human FN3KRP and/or human FN3K gene in a sample that has been confirmed as having the ability to phosphorylate in vivo the compound represented by general formula (I), so as to examine the ability of the subject to phosphorylate the compound represented by general formula (I).

(2) Method Using Expression Level of Human FN3KRP and/or Human FN3K Protein as Indicator This method comprises the following steps (i) and (ii):
(i) measuring the expression level of a human FN3KRP and/or human FN3K protein in a sample collected from a subject, using an antibody or a ligand specifically binding to the aforementioned protein; and
(ii) comparing the expression level of the human FN3KRP and/or human FN3K protein measured in (i) above with the expression level of the human FN3KRP and/or human FN3K protein in a sample that has been confirmed as having the ability to phosphorylate in vivo the compound represented by general formula (I), so as to examine the ability of the subject to phosphorylate the compound represented by general formula (I).

(3) Method Using Enzyme Activity of Human FN3KRP and/or Human FN3K Protein as Indicator This method comprises the following steps (i) and (ii):
(i) measuring the enzyme activity of a human FN3KRP and/or human FN3K protein in a sample collected from a subject; and
(ii) comparing the enzyme activity of the human FN3KRP and/or human FN3K protein measured in (i) above with the enzyme activity of the human FN3KRP and/or human FN3K protein in a sample that has been confirmed as having the ability to phosphorylate in vivo the compound represented by general formula (I), so as to examine the ability of the subject to phosphorylate the compound represented by general formula (I).

(4) Method Using Genetic Mutation
(i) determining the nucleotide sequence of human FN3KRP and/or human FN3K in a human FN3KRP and/or human FN3K gene in a sample collected from a subject;
(ii) examining in the nucleotide sequence of the human FN3KRP and/or human FN3K gene the presence or absence of a mutation that influences enzyme activity; and
(iii) determining that a subject having in the nucleotide sequence a mutation that decreases the activity of the human FN3KRP and/or human FN3K gene has only a low ability to phosphorylate the compound represented by general formula (I), and determining that a subject who has in the nucleotide sequence no mutation that decreases the activity of the human FN3KRP and/or human FN3K gene has the ability to phosphorylate the compound represented by general formula (I).

9. Diagnostic Kit

Human FN3K and/or human FN3KRP has the ability to phosphorylate a compound that is activated by being phosphorylated in vivo. Accordingly, using the following kit, the ability of a subject to metabolize a drug can be examined. Specifically, the kit is as follows.

A kit for diagnosing ability to metabolize a drug, which comprises at least one selected from the group consisting of the following (1) to (5):

(1) an oligonucleotide primer comprising 15 to 30 contiguous nucleotides that is used for specifically amplifying a part of or the entire polynucleotide having the nucleotide sequence as shown in SEQ ID NO: 1 or 3 in the sequence listing;

(2) a polynucleotide probe comprising 15 or more contiguous nucleotides that hybridizes under stringent conditions with the polynucleotide having the nucleotide sequence as shown in SEQ ID NO: 1 or 3 in the sequence listing, for detecting the above described polynucleotide;

(3) a solid-phase sample, having a polynucleotide selected from either the oligonucleotide primer described in (1) above or the polynucleotide probe described in (2) above immobilized thereon;

(4) an antibody that specifically binds to a polypeptide selected from the following (a) to (c), so as to detect the protein:
(a) a polypeptide having the amino acid sequence of amino acid Nos. 1-309 of SEQ ID NO: 2 in the sequence listing;
(b) a polypeptide having the amino acid sequence of amino acid Nos. 1-309 of SEQ ID NO: 4 in the sequence listing; and
(c) a polypeptide having an amino acid sequence comprising a deletion, substitution or addition of one or several amino acids with respect to the amino acid sequence of a polypeptide selected from the above (a) and (b), and having the ability to phosphorylate (2R)-2-amino-2-methyl-4-[5-(5-phenylpentanoyl)thiophen-2-yl]butan-1-ol; and (5) a secondary antibody that binds to the antibody described in (4) above.

EXAMPLES

The present invention will be described in the following examples. However, these examples are not intended to limit the scope of the present invention. In the following examples, procedures for genetic manipulation were carried out according to the methods described in Molecular Cloning, Sambrook, J., Fritsch, E. F. and Maniatis, T., Cold Spring Harbor Laboratory Press, 1989, and other experimental manuals, and also according to methods known to persons skilled in the art, unless otherwise specified. Where commercially available reagents or kits are used, the procedures were carried out according to the instruction manuals included with those commercially available products.

Reference Example

Obtainment of (2R)-2-amino-2-methyl-4-[5-(5-phenylpentanoyl)thiophen-2-yl]butan-1-ol (2R)-2-amino-2-methyl-4-[5-(5-phenylpentanoyl) thiophen-2-yl]butan-1-ol (hereinafter also referred to as "compound 1") represented by general formula (I), which will be used in the following experiment, can be produced by the methods described, for example, in International Publication WO94/08943 pamphlet, International Publication WO96/06068 pamphlet, International Publication WO98/45249 pamphlet, International Publication WO03/029184 pamphlet, International Publication WO03/029205 pamphlet, International Publication WO02/06268 pamphlet (Example 19), International Publication WO03/059880 pamphlet, International Publication WO05/005383 pamphlet, International Publication WO05/063671 pamphlet, etc.

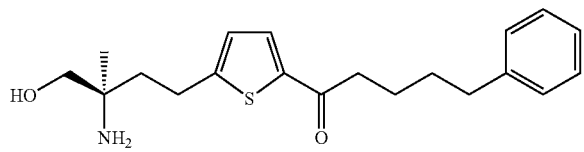

(I)  (2R)-2-amino-2-methyl-4-[5-(5-phenylpentanoyl)thiophen-2-yl]butan-1-ol (compound 1)

Example 1

Preparation of Human Whole Blood

Approximately 100 mL each of peripheral blood was collected from each of two anonymous blood donors. Approximately 11 mL of a 3.2% (w/v) trisodium citrate bihydrate aqueous solution was added as an anticoagulant to 100 mL of the human peripheral blood, so as to prepare human whole blood. Thereafter, the human whole blood was fractionated into fractions such as erythrocyte, plasma, thrombocyte and lymphocyte according to an ordinary method.

Example 2

Confirmation of Phosphorylating Activity and Localization of Phosphorylating Activity The phosphorylating activity of each constitutional component obtained in Example 1 to compound 1 was measured. Compound 1 was used as a reaction substrate and phosphorylating activity was measured by quantifying the amount of phosphoric acid mono(2R) -2-amino-2-methyl-4-[5-(5-phenylpentanoyl)thiophen-2-yl]butyl ester (the phosphoric ester of compound 1) generated as a reaction product.

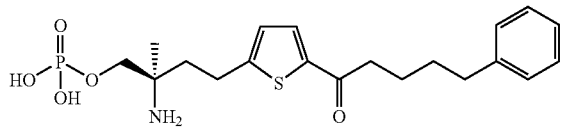

Phosphoric Acid mono(2R)-2-amino-2-methyl-4-[5-(5-phenylpentanoyl)thiophen-2-yl]butyl ester Thirteen 1.5-mL polypropylene tubes were prepared. The whole blood, plasma, erythrocyte, thrombocyte and lymphocyte obtained in Example 1 were used singly or in combinations, such as whole blood, plasma, erythrocyte, thrombocyte, lymphocyte, erythrocyte+plasma, thrombocyte+plasma, lymphocyte+plasma, erythrocyte+thrombocyte+lymphocyte+plasma, erythrocyte+thrombocyte+lymphocyte, erythrocyte+thrombocyte+plasma, erythrocyte+lymphocyte+plasma, and thrombocyte+lymphocyte+plasma. These combinations of constitutional blood components were dispensed in the tubes, followed by cooling on ice. The dispensed amount of the blood component dispensed into each tube was always set at 500 μL. When two or more constitutional components were mixed, equal amounts of the components were mixed to a total amount of 500 of μL. That is, when two types of constitutional components were mixed, 250 μL of each component was dispensed. When three types of components were mixed, 166.7 μL of each component was dispensed. When four types of components were mixed, 125 μL of each component was dispensed. Thus, the total amount was always set at 500 μL. 0.5 μL of a 100 mg/mL compound 1/dimethyl sulfoxide solution was added to each tube, followed by blending (final concentration: 100 μg/mL). Thereafter, the solution was cooled on ice, and it was then incubated in a hot-water bath at 37° C. for 30 minutes. Thereafter, the tube was transferred onto ice. 1 mL of methanol was added to each tube, and they were then mixed. Thereafter, the resultant solution was preserved at −20° C. until HPLC measurement was carried out.

The amount of phosphoric acid mono(2R)-2-amino-2-methyl-4-[5-(5-phenylpentanoyl)thiophen-2-yl]butyl ester (the phosphoric ester of compound 1) generated as a reaction product was measured using the following apparatus under the following conditions.

HPLC: LC-10A$_{vp}$ system (Shimadzu Corp.)
Column: YMC-Pack ODS-A A-312 (6.0 mm (diameter)×150 mm (length); particle size: 5 μm; YMC)
Mobile phase: 40% acetonitrile/0.1% trifluoroacetic acid
Flow rate: 1 mL/min
Elution method: Isocratic elution
Column temperature: 40° C.
Detection wavelength: 295 nm
Retention time: 6.7 minutes (the phosphoric ester of compound 1); 11.1 minutes (compound 1); 14.2 minutes (1-naphthol, an internal standard substance)

After completion of the reaction, a 10 μg/mL 1-naphthol/methanol solution was added to the tube to a final concentration of 2.5 μg/mL. Thereafter, the obtained mixture was centrifuged at 21,600×g at 4° C. for 3 minutes. Thereafter, 30 μL of the supernatant was loaded on the aforementioned HPLC apparatus, and the AUC value of a peak appearing during each retention time was measured. The AUC value of the compound was calibrated with the AUC value of 1-naphthol used as an internal standard substance, and it was then extrapolated through a calibration curve, which had been produced separately, so as to obtain the concentration of the compound.

As a result of the measurement, as shown in FIG. 1, when erythrocytes were present in the reaction system, the amount of phosphoric ester of compound 1 generated became high, and thus it was revealed that compound 1 had been phosphorylated. Accordingly, it became clear that, among the constitutional components in the whole blood, erythrocytes play a main role in phosphorylating compound 1.

Example 3

Localization of Enzyme that Phosphorylates Compound 1 in Human Erythrocytes

Erythrocytes were fractionated into a soluble fraction and a membrane fraction according to an ordinary method. The reaction of phosphorylating compound 1 was examined by the same method as that described in Example 2. As shown in FIG. 2, it was confirmed that strong phosphorylating activity was present in the erythrocyte soluble fraction. Thus, it was revealed that an enzyme that phosphorylates compound 1 is mainly present in the erythrocyte soluble fraction.

Example 4

Purification of Enzyme that Phosphorylates Compound 1 from Human Erythrocyte Soluble Fraction (1)

An enzyme that phosphorylates compound 1 was purified from a human erythrocyte soluble fraction according to the following method.

(1) Enzyme Activity Measurement Method

100 μg/mL compound 1, 1 mM ATP, 0.5% CHAPS, and 100 mM HEPES (pH 7.0) were added to 45 μL of a sample used in the measurement of enzyme activity, to a total amount of 75 μL. When 1-deoxy-1-morpholinofructose (DMF; Sigma) was added to the reaction solution, it was added thereto to a final concentration of 1 mM. The mixed solution was incubated at 37° C. for 1 hour, so as to phosphorylate compound 1. Thereafter, 150 μL of methanol was added to the reaction solution, and the mixture was then filtrated through a filter with a pore diameter of 0.45 μm, so as to terminate the reaction and remove the protein. 10 μL of the filtrate was subjected to a reverse phase chromatography column (TSK-gel ODS-100S; 4.6 mm (diameter)×150 mm (length); Tosoh Corp). Isocratic elution was carried out using 40% acetonitrile comprising 0.1% trifluoroacetic acid at a flow rate of 1 mL/min at a column temperature of 40° C. Compound 1 and phosphoric ester of compound 1 generated were detected at 295 nm. The amount of phosphoric ester of compound 1 generated was measured based on a peak area. The activity necessary for generating 1 μg/mL phosphoric ester of compound 1 under the aforementioned conditions was defined as 1 U/mL. In the subsequent purification process, in order to measure the activity of an enzyme that phosphorylates compound 1, the present measurement method was used.

(2) Purification of Enzyme that Phosphorylates Compound 1 from Human Erythrocyte Soluble Fraction 100 mL each of blood was collected from five anonymous volunteers, so that a total of 500 mL of blood was collected. Using the activity of phosphorylating compound 1 as an indicator, an erythrocyte soluble fraction prepared according to an ordinary method was purified using each of ammonium sulfate salting-out, a hydrophobic interaction column (Hi-Trap Phenyl HP 5 mL, GE Healthcare Biosciences), a dye-binding affinity column (HiTrap Blue HP 1 mL, GE Healthcare Biosciences), an anion exchange column (Resource Q 1 mL, GE Healthcare Biosciences), a cation exchange column (Resource S 1 mL, GE Healthcare Biosciences), a cation exchange column (Mono S PC 1.6/5, GE Healthcare Biosciences), and a gel filtration column (Superdex 75 PC 3.2/30, GE Healthcare Biosciences). As a result, the activity of phosphorylating compound 1 in the human erythrocyte soluble fraction was concentrated to approximately 10,000 times, as shown in Table 1.

Example 5

Identification of Enzyme that Phosphorylates Compound 1 by Mass Spectrometry (1)

The active fraction obtained in Example 4 was subjected to SDS-PAGE, and each band was then cut out of the SDS-PAGE gel. According to an ordinary method, trypsin (modified trypsin, Promega) was added thereto, and a digestion reaction was then carried out at 37° C. for 12 hours. The digested peptide was subjected to liquid chromatography (LC)/tandem mass spectrograph (MS/MS). The obtained mass spectrometry data was analyzed by database-searching software (Mascot, Matrix Science). As database, GenBank nr database collected by the National Center for Biotechnology Information was used.

As a result, it was revealed that the enzyme that phosphorylates compound 1 is human sequence fructosamine-3-kinase (FN3K, GenBank Accession No. NP_071441).

Example 6

Purification of Enzyme that Phosphorylates Compound 1 from Human Erythrocyte Soluble Fraction (2)

In order to confirm that human FN3K is an enzyme that phosphorylates compound 1, an inhibition experiment was carried out using DMF that has been known as a competitive inhibitor of the human FN3K (Biochem. J. (2000) Vol. 352, pp. 835-839). The active fraction of the hydrophobic interaction column at the second purification stage in Example 4 was significantly inhibited by DMF, and the $IC_{50}$ value thereof was approximately 1 μM. Thus, it was confirmed that human FN3K is an enzyme that phosphorylates compound 1.

On the other hand, in the case of a soluble fraction and a sample obtained by re-solubilizing the ammonium sulfate precipitate obtained at the first purification stage, such inhibition by DMF was hardly observed. Thus, the presence of another enzyme for phosphorylating compound 1 that differs from human FN3K was strongly suggested. Considering the degree of inhibition by DMF, it was assumed that this enzyme differing from human FN3K is an enzyme that mainly phosphorylates compound 1. Hence, this enzyme was then purified.

For purification, enzyme activity was always measured in the presence and absence of 1 mM DMF, so that the purification was carried out using activity that is not inhibited by DMF as an indicator.

TABLE 1

Purification table of human FN3K

| Purification step | Protein concentration [μg/mL] | Activity [U/mL] | Volume [mL] | Total protein amount [mg] | Total activity [U] | Specific activity [U/mg] | Purification efficiency | Activity recovery rate [%] |
| --- | --- | --- | --- | --- | --- | --- | --- | --- |
| Soluble fraction | 83000 | 3.2 | 50 | 4100 | 160 | 0.039 | 1.0 | 100 |
| 1) Ammonium sulfate precipitation | 9000 | 7.3 | 50 | 450 | 367 | 0.81 | 21 | 230 |
| 2) Hydrophobic interaction column | 170 | 1.7 | 60 | 10 | 100 | 10 | 260 | 63 |
| 3) Dye-binding affinity column | 870 | 5.1 | 4.0 | 3.5 | 20 | 5.9 | 150 | 13 |
| 4) Anion exchange column | 210 | 2.1 | 10 | 2.1 | 21 | 10 | 260 | 13 |
| 5) Cation exchange column | 87 | 2.8 | 4.0 | 0.35 | 11 | 32 | 820 | 6.9 |
| 6) Cation exchange column | 10 | 7.1 | 0.20 | 0.0020 | 1.4 | 710 | 18000 | 0.88 |
| 7) Gel filtration column | 4.0 | 1.6 | 0.10 | 0.00040 | 0.16 | 410 | 10000 | 0.10 |

The ammonium sulfate precipitate obtained in Example 4 was fractionated by each of an anion exchange column (HiPrep Q 16/10 XL, GE Healthcare Biosciences), a dye-binding affinity column (HiTrap Blue HP 1 mL), a cation exchange column (Mono S PC 1.6/5), and a gel filtration column (Superdex 75 PC 3.2/30).

As a result of the aforementioned 5-step purification process, as shown in Table 2, the enzyme activity after the second purification step was not inhibited by DMF, and the specific activity of the enzyme that phosphorylates compound 1 was finally increased to approximately 16,000 times by this purification method.

TABLE 2

Purification table of human FN3KRP

| Purification step | Protein concentration [µg/mL] | Activity [U/mL] | Volume [mL] | Total protein amount [mg] | Total activity [U] | Specific activity [U/mg] | Purification efficiency | Activity recovery rate [%] | Remaining activity [%] |
|---|---|---|---|---|---|---|---|---|---|
| Soluble fraction | 100000 | 3.0 | 50 | 5200 | 150 | 0.029 | 1.0 | 100 | 81 |
| 1) Ammonium sulfate precipitation | 9100 | 5.0 | 50 | 460 | 250 | 0.55 | 19 | 170 | 89 |
| 2) Anion exchange column | 640 | 5.5 | 10 | 6.4 | 55 | 8.7 | 300 | 36 | 98 |
| 3) Dye-binding affinity column | 310 | 10 | 1.0 | 0.31 | 10 | 32 | 1100 | 6.6 | 110 |
| 4) Cation exchange column | 5.0 | 8.5 | 0.20 | 0.00010 | 1.7 | 1700 | 58000 | 1.1 | 98 |
| 5) Gel filtration column | 3.0 | 1.4 | 0.10 | 0.00030 | 0.14 | 450 | 16000 | 0.090 | Unmeasured |

Remaining activity: (enzyme activity in presence of 1 mM DMF) ÷ (enzyme activity in absence of DMF) × 100(%)

Example 7

Identification of Enzyme that Phosphorylates Compound 1 by Mass Spectrometry (2)

Bands around 33 kDa obtained by subjecting the purified active fraction to SDS-PAGE were subjected to mass spectrometry, so as to identify the proteins of these bands. As a result, it was confirmed that all these bands were identical to a human sequence hypothetical fructosamine kinase-like protein (FN3KRP, which has been registered in the protein database of GenBank under Accession No. Q9HA64).

The molecular weight predicted from the sequence of human FN3KRP was found to be 35 kDa, and this molecular weight was almost identical to the putative molecular weight obtained by SDS-PAGE (33 kDa) and the putative molecular weight obtained by gel filtration (24-38 kDa).

Accordingly, it became clear that the enzyme phosphorylating compound 1, which was purified in the present example, was human FN3KRP.

Example 8

Construction of Human FN3KRP Expression Vector

The cDNA clone (Clone ID: 3351601) of human FN3KRP purchased from Invitrogen was treated with restriction enzymes XhoI and EcoRI, so as to extract cDNA. This cDNA was then allowed to bind to a plasmid vector treated with XhoI and EcoRI, namely, pcDNA3.1(+)neo (Invitrogen). Thereafter, Escherichia coli DH5α was transformed with the plasmid as a binding reaction product. The obtained transformant was cultured in a large amount, so as to obtain an expression plasmid vector containing the cDNA of human FN3KRP, hFN3KRP/pcDNA3.1(+)neo.

Example 9

Construction of Human FN3K Expression Vector

Using Gateway Technology (Invitrogen), cDNA was transferred from the cDNA clone (catalog No. GC-W1392) of human FN3K purchased from GeneCopoeia to an expression plasmid vector used for mammalian cells, pcDNA3.2-DEST. After completion of the reaction, Escherichia coli DH5α was transformed with the obtained DNA solution. The obtained transformant was cultured in a large amount, so as to obtain an expression plasmid vector containing the cDNA of human FN3K, hFN3K/pcDNA3.2-DEST.

Example 10

Gene Introduction Using Human FN3KRP/FN3K Expression Vector and Preparation of Cytoplasmic Fraction from Transient Expression Cells In order to confirm that human FN3KRP and human FN3K actually have activity of phosphorylating compound 1, an expression vector of each gene was introduced into the cultured cells, so that it was allowed to transiently express therein, thereby preparing the cytoplasmic fraction thereof.

HEK293 cells were inoculated to three 75-cm$^2$ culture flasks, and they were then cultured until they became 80% confluent. Using a lipofectamine plus reagent (Invitrogen), gene introduction was carried out without plasmid DNA, with 4 µg of hFN3KRP/pcDNA3.1(+)neo, and with 4 µg of hFN3K/pcDNA3.2-DEST, for each of the three flasks. Thereafter, the cells were cultured for approximately 27 hours. Thereafter, the cells were washed with PBS, and 2.5 mL of a cell lysate (100 mM HEPES (pH 7.4), 80% (v/v) CelLytic-M (Sigma), 1 mM dithiothreitol, a single protease inhibitor cocktail for 50 mL (Complete EDTA-free, Roche)) was then added to the cells. Thereafter, the cells were intensively shaken, until all of them were removed. The thus removed cells and the supernatant were recovered, and they were then ultracentrifuged at 20,000×g at 4° C. for 15 minutes. Thereafter, the supernatant was recovered, and aliquots each of 200 µL were frozen in liquid nitrogen. They were preserved at −80° C. until used. In addition, a portion of the supernatant was subjected to measurement of protein concentration.

Example 11

Measurement of Activity of Cytoplasmic Fraction to Phosphorylate Compound 1

Each of the components was added to a 1.5-mL polypropylene tube to the following final concentrations, with the total amount set at 250 µL, followed by leaving the obtained solution at rest on ice (100 mM HEPES (pH 7.4), 5 mM magnesium chloride, 1 mM ATP, 1 mM dithiothreitol, 0.5% CHAPS, 100 µg/mL compound 1, and each cytoplasmic fraction obtained in Example 10 in an amount of 18.2, 54.6, and 163.8 µg or not added). The obtained mixture was incubated in a hot-water bath at 37° C. for 3 hours, and was then transferred onto ice. 0.5 mL methanol was added to each tube, and mixed with the reaction product. Thereafter, the mixture was preserved at −20° C. until HPLC measurement was carried out.

The amount of phosphoric ester of compound 1 generated was measured by the method described in Example 2. As a result, as shown in FIG. 3, the phosphoric ester of compound 1 was generated only when the cytoplasmic fraction in which human FN3KRP or human FN3K had been expressed was used. From the aforementioned results, it became clear that human FN3KRP and human FN3K in fact have activity to phosphorylate compound 1.

Example 12

Confirmation of Ability to Phosphorylate FTY720 and Sphingosine

Sphingosine kinase 1 and 2 are enzymes that convert sphingosine to sphingosine-1-phosphate (S1P) in vivo. It has been known that these enzymes phosphorylate FTY720 to generate an FTY720 phosphoric ester.

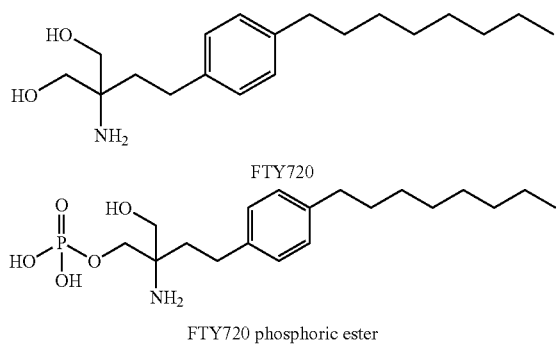

(J Biol Chem. (2003) Vol. 278, pp. 47408-47415) (FEBS Lett. (2003) Vol. 554, pp. 189-193)

It was thus analyzed whether or not by contrast human FN3KRP and human FN3K act to phosphorylate FTY720 or sphingosine.

Eighteen 1.5-mL polypropylene tubes were prepared. Components were added to each tube to the following final concentrations, with the total amount set at 250 µL, followed by leaving the obtained solution at rest on ice (100 mM HEPES (pH 7.4), 5 mM magnesium chloride, 5 mM ATP, 1 mM dithiothreitol, 0.5% CHAPS, 10 µM FTY720 or sphingosine, each cytoplasmic fraction obtained in Example 10 in an amount of approximately 91 µg). The obtained mixture was incubated in a hot-water bath at 37° C. for 3 hours, and was then transferred onto ice. 0.5 mL methanol was added to each tube, and mixed with the reaction product. Thereafter, the mixture was preserved at −20° C. until LC/MS/MS measurement was carried out.

The amount of FTY720 phosphoric ester or S1P generated was analyzed using the following LC/MS/MS system.
LC system:
HPLC apparatus name: Agilent 1100 series (Agilent Technologies)
Autosampler name: HTC PAL (CTC Analytics)

MS/MS system:
Apparatus name: API4000 (Applied Biosystems/MDS Sciex)

As a result, it was found that both the human FN3KRP and the human FN3K slightly phosphorylate FTY720, but that they do not have ability to phosphorylate sphingosine (FIG. 4). Accordingly, it became clear that the human FN3KRP and the human FN3K are enzymes that phosphorylate compound 1 and FTY720.

Example 13

Reaction of Phosphorylating Compound 1 and its Analogs Using Human FN3KRP Expression Cytoplasmic Fraction The following compounds were phosphorylated using the human FN3KRP expression cytoplasmic fraction prepared in Example 10:
(2R)-2-amino-2-methyl-4-[5-(5-phenylpentanoyl)thiophen-2-yl]butan-1-ol (compound 1);
2-amino-2-[4-(3-benzyloxyphenylthio)-2-chlorophenyl] propyl-1,3-propanediol (ROX-2127);
(2R)-2-amino-2-methyl-4-[1-methyl-5-(5-phenylpentanoyl) pyrrol-2-yl]butan-1-ol (compound 2);
(2R)-2-amino-2-methyl-4-{1-methyl-5-[4-(4-methylphenyl) butanoyl]pyrrol-2-yl}butan-1-ol, (compound 3);
(2R)-2-amino-2-methyl-4-{3-methyl-5-[4-(3,4-dimethylphenyl)butanoyl]thiophen-2-yl}butan-1-ol (compound 4);
(2R)-2-amino-2-methyl-4-{3-methyl-5-[4-(3,4-dimethoxyphenyl)butanoyl]thiophen-2-yl}butan-1-ol (compound 5);
(2R)-2-amino-2-methyl-4-{1-methyl-5-[4-(3,4-dimethylphenyl)butanoyl]pyrrol-2yl}butan-1-ol (compound 6);
(2R)-2-amino-2-methyl-4-{3-chloro-5-[4-(3,4-dimethylphenyl)butanoyl]thiophen-yl}butan-1-ol (compound 7);
(2R)-2-amino-2-methyl-4-{1,3-dimethyl-5-[4-(3,4-dimethylphenyl)butanoyl]pyrrol-2-yl}butan-1-ol (compound 8);
(2R)-2-amino-2-methyl-4-{1-methyl-3-chloro-5-[4-(3,4-dimethoxyphenyl)butanoyl]pyrrol-2-yl}butan-1-ol (compound 9);
(2R)-2-amino-2-methyl-4-{1,3-dimethyl-5-[4-(3,4-dimethoxyphenyl)butanoyl]pyrrol-2-yl}butan-1-ol (compound 10);
2-amino-2-methyl-3-(4-heptanoylphenoxy)propan-1-ol (compound 11);
(2R)-2-amino-2-methyl-5-{1-methyl-5-[4-(4-methylphenyl) butanoyl]pyrrol-2-yl}pentan-1-ol (compound 12);
(2R)-2-amino-2-methyl-5-{5-[4-(4-methylphenyl)butanoyl] thiophen-2-yl}pentan-1-ol (compound 13);
2-amino-2-methyl-3-{4-[4-(4-methylphenyl)butanoyl] phenylmethoxyl}propan-1-ol (compound 14);
2-amino-2-methyl-3-{2-chloro-4-[4-(4-methylphenyl)butanoyl]phenylmethoxyl}propan-1-ol (compound 15); and
2-amino-2-methyl-3-{5-[4-(3,4-dimethylphenyl)butanoyl] thiophen-2-ylmethoxyl}propan-1-1 (compound 16).

Reaction solution: 100 mM HEPES (pH 7.4), 5 mM magnesium chloride, 5 mM ATP, 1 mM dithiothreitol, 0.5% CHAPS, and 0.328 mg/mL human FN3KRP expression cytoplasmic fraction
Reaction volume: 100 µL
Reaction substrate: 100 µM
Reaction condition: 37° C., 3 hours After completion of the reaction, 200 µL of methanol was added to the reaction solution, and the mixture was then stirred. The mixed solution was centrifuged (16,000×g, 10 minutes, 4° C.), and 20 µL of the supernatant was then subjected to HPLC, so that analysis was carried out under the following conditions.

HPLC apparatus: HP1100 (Agilent Technologies)
Column: YMC-pack ODS A-312
Column temperature: 40° C.
Flow rate: 1 mL/min
Mobile phase: 30% acetonitrile (0.1% trifluoroacetic acid)→90% acetonitrile (0.1% trifluoroacetic acid)
Elution method: Gradient elution was carried out. The initial acetonitrile concentration and gradient inclination were changed depending on the type of compound. A typical elution method comprises the following conditions:
30% acetonitrile (0.1% trifluoroacetic acid)
90% acetonitrile (0.1% trifluoroacetic acid)
Gradient inclination: 2% acetonitrile/min
Detection wavelength: 295 nm, 254 nm, or 230 nm
The efficiency of phosphorylating each compound was calculated using the peak areas of phosphoric ester and unreacted substrate, as shown in the following formula.

Phosphorylation efficiency (%)=peak area of phosphoric ester/(peak area of phosphoric ester+peak area of unreacted substrate)×100

As a result of the aforementioned measurement, it was confirmed that human FN3KRP is an enzyme that phosphorylates various types of compounds (Table 3).

TABLE 3

Phosphorylation efficiency of human FN3KRP

| Compound | Phosphorylation efficiency (%) |
|---|---|
| Compound 1 | 97.6 |
| ROX-2127 | 37.5 |
| Compound 2 | 95.6 |
| Compound 3 | 91.5 |
| Compound 4 | 32.6 |
| Compound 5 | 38.3 |
| Compound 6 | 95.2 |
| Compound 7 | 44.7 |
| Compound 8 | 3.3 |
| Compound 9 | 10.6 |
| Compound 10 | 4.8 |
| Compound 11 | 14.9 |
| Compound 12 | 97.5 |
| Compound 13 | 98.6 |
| Compound 14 | 34.0 |
| Compound 15 | 18.1 |
| Compound 16 | 29.1 |

Example 14

Reaction of Phosphorylating Compound 1 and its Analogs Using Human FN3K Expression Cytoplasmic Fraction A reaction of phosphorylating the same compound 1 and the same analogs thereof as used in Example 13 was carried out under the following conditions, using the human FN3K expression cytoplasmic fraction prepared in Example 10.
Reaction solution: 100 mM HEPES (pH 7.4), 5 mM magnesium chloride, 5 mM ATP, 1 mM dithiothreitol, 0.5% CHAPS, and 0.3 mg/mL human FN3K expression cytoplasmic fraction
Reaction volume: 100 µh
Reaction substrate: 100 µM
Reaction condition: 37° C., 3 hours After completion of the reaction, 200 µL of methanol was added to the reaction solution, and the mixture was then stirred. The mixed solution was centrifuged (16,000×g, 10 minutes, 4° C.), and 20 µL of the supernatant was then subjected to HPLC, so that analysis was carried out under the conditions described in Example 13. The efficiency of phosphorylating each analog was calculated using the formula as shown in Example 13.

As a result, it was confirmed that human FN3K is an enzyme that phosphorylates compound 1 and analogs thereof (Table 4).

TABLE 4

Phosphorylation efficiency of human FN3K

| Compound | Phosphorylation efficiency (%) |
|---|---|
| Compound 1 | 28.1 |
| ROX-2127 | 0.0 |
| Compound 2 | 17.9 |
| Compound 3 | 16.4 |
| Compound 4 | 4.7 |
| Compound 5 | 4.9 |
| Compound 6 | 19.3 |
| Compound 7 | 5.4 |
| Compound 8 | 0.0 |
| Compound 9 | 2.2 |
| Compound 10 | 0.0 |
| Compound 11 | 0.0 |
| Compound 12 | 24.8 |
| Compound 13 | 23.3 |
| Compound 14 | 0.0 |
| Compound 15 | 0.0 |
| Compound 16 | 3.4 |

Example 15

Reaction of Phosphorylating Compound 1 and its Analogs Using Rat Erythrocytes

Erythrocytes were prepared from Wistar-Imamichi rats (purchased from Institute for Animal Reproduction) in the same manner as in Example 1. A reaction of phosphorylating the same compound 1 and the same analogs thereof as in Example 13 was carried out under the following conditions, using these rat erythrocytes.

Reaction solution: Rat erythrocytes
Reaction volume: 500 µh
Reaction substrate: 100 µg/mL
Reaction condition: 37° C., 3 hours After completion of the reaction, 1 mL of methanol was added to the reaction solution, and the mixture was then stirred. The mixed solution was centrifuged (16,000×g, 5 minutes, 4° C.). The supernatant was centrifuged again (16,000×g, 10 minutes, 4° C.), and 20 µL of a newly obtained supernatant was then subjected to HPLC, so that analysis was carried out under the conditions described in Example 13. The efficiency of phosphorylating each analog was calculated using the formula as shown in Example 13.

As a result, it was confirmed that rat erythrocytes phosphorylate compound 1 and analogs thereof (Table 5).

TABLE 5

Phosphorylation efficiency of rat erythrocytes

| Compound | Phosphorylation efficiency (%) |
|---|---|
| Compound 1 | 96.5 |
| ROX-2127 | 31.7 |
| Compound 2 | 72.0 |
| Compound 3 | 61.4 |
| Compound 4 | 17.5 |
| Compound 5 | 45.9 |
| Compound 6 | 66.2 |
| Compound 7 | 25.9 |
| Compound 8 | 3.6 |
| Compound 9 | 13.3 |
| Compound 10 | 7.7 |
| Compound 11 | 44.6 |
| Compound 12 | 73.4 |
| Compound 13 | 82.2 |
| Compound 14 | 45.4 |
| Compound 15 | 31.6 |
| Compound 16 | 39.0 |

The series of experiments conducted in Examples 1 to 15 demonstrated that human FN3KRP and human FN3K are present in human erythrocytes, and that these are enzymes that phosphorylate compound 1, analogs thereof, and FTY720.

INDUSTRIAL APPLICABILITY

The present invention is able to elucidate an enzyme that phosphorylates in vivo a compound such as (2R)-2-amino-2-methyl-4-[5-(5-phenylpentanoyl)thiophen-2-yl]butan-1-ol, and to provide a method of phosphorylating the aforementioned compound using the aforementioned enzyme. In addition, the present invention is also able to provide a method of screening for a substance phosphorylated by the aforementioned enzyme. Moreover, the invention is also able to provide a method of determining the ability of a subject to phosphorylate a test compound. Furthermore, the invention is also able to provide a method of determining the ability of a subject to metabolize a drug, using the phosphorylating ability of the present enzyme as an indicator.

Figure 1:
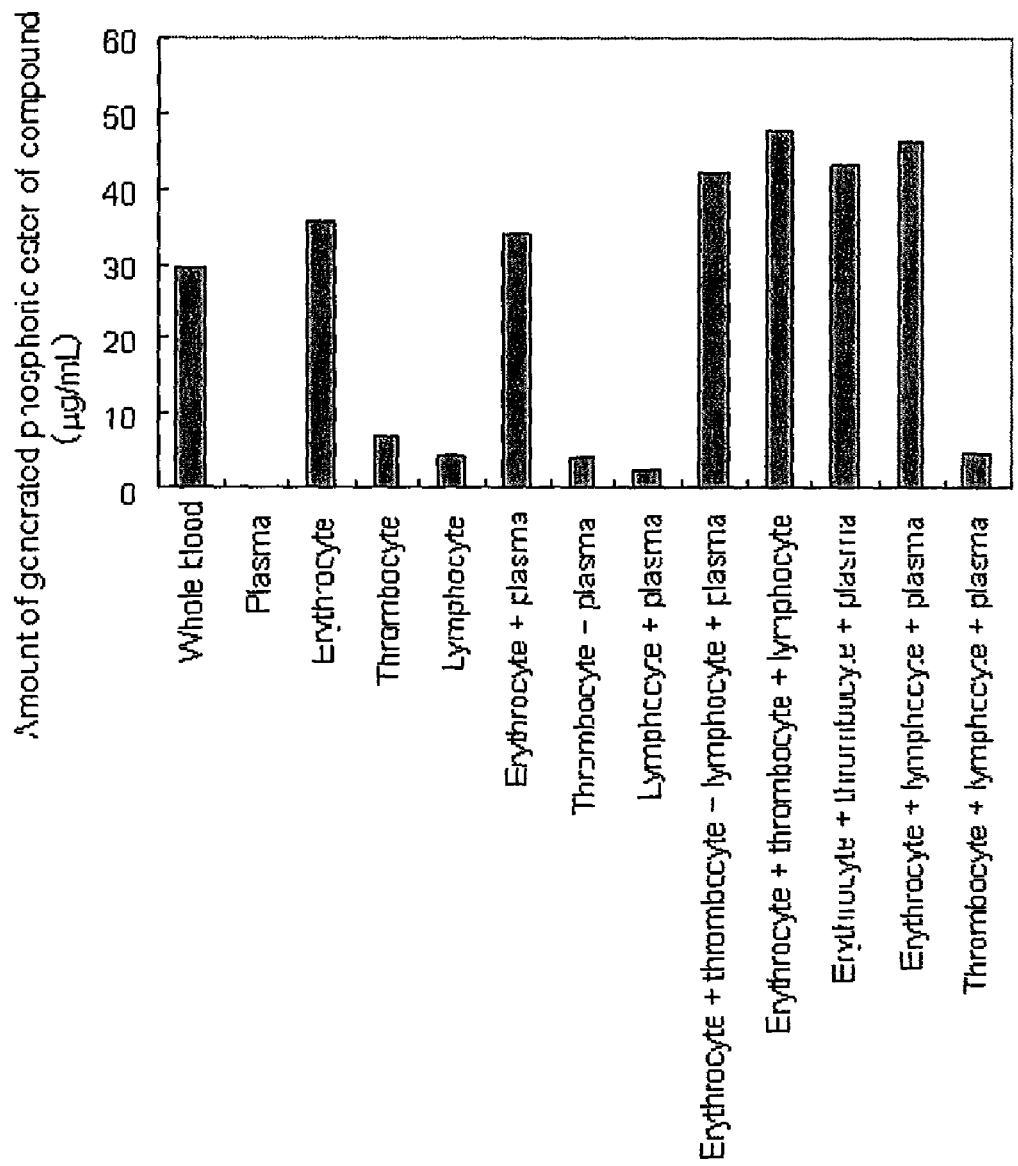
FIG. 1 shows phosphorylation of compound 1 by each constitutional component existing in human blood.
Figure 2:
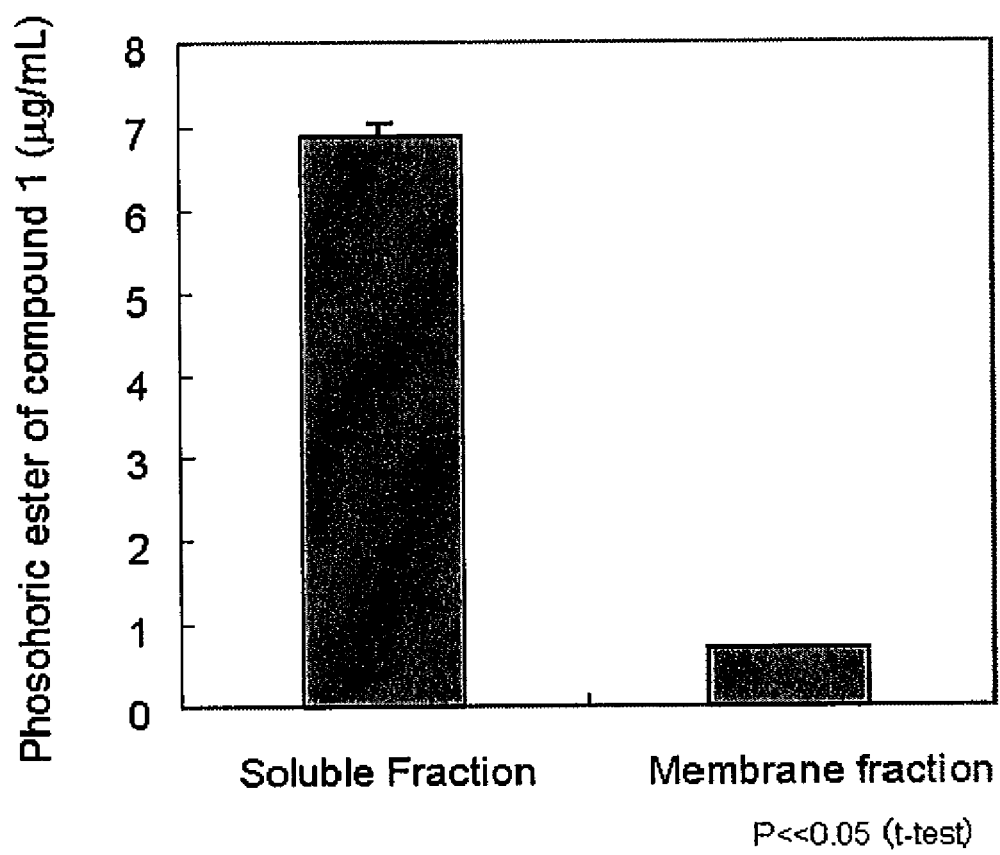
FIG. 2 shows the concentration of reaction product in each fraction.
Figure 3:
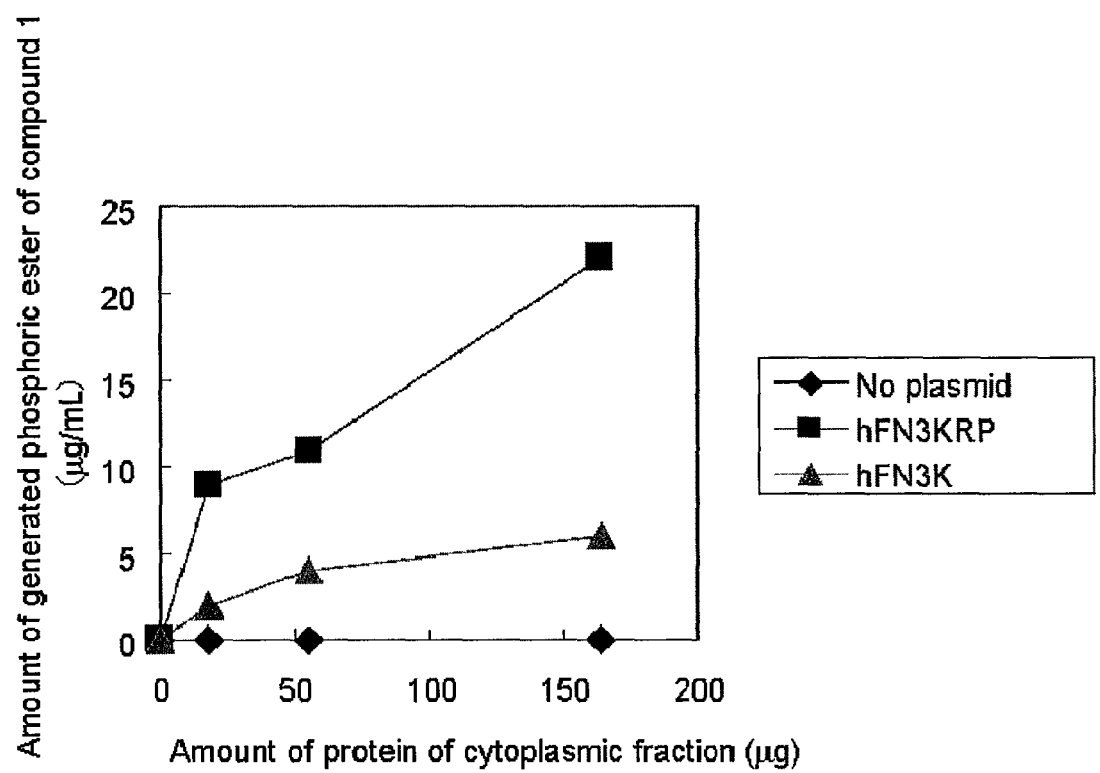
FIG. 3 shows the activity to phosphorylate compound 1.
Figure 4:
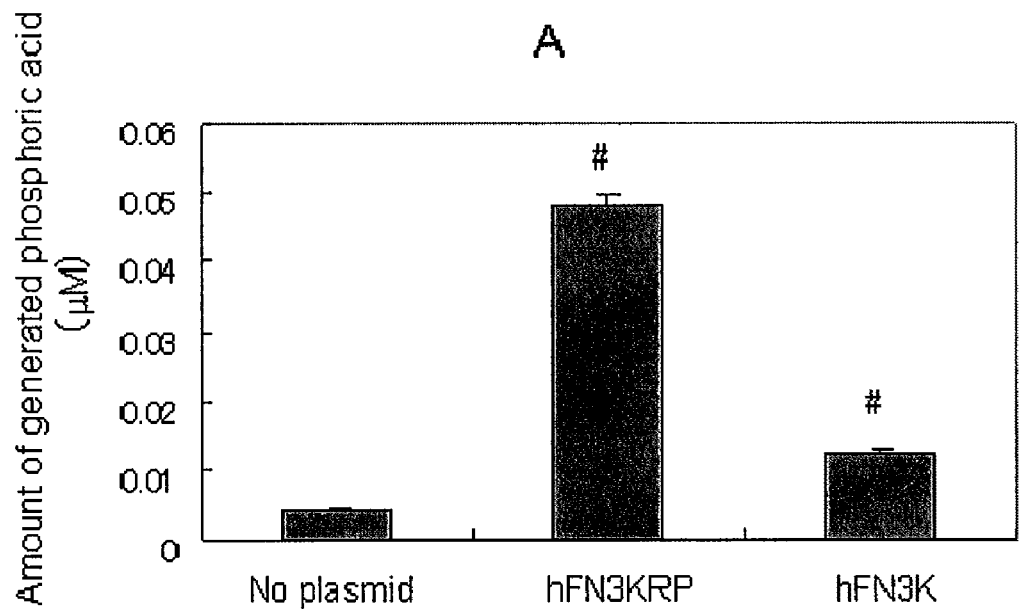
FIG. 4(A) shows phosphorylation of FTY720.
FIG. 4(B) shows phosphorylation of sphingosine.
Figure 4:
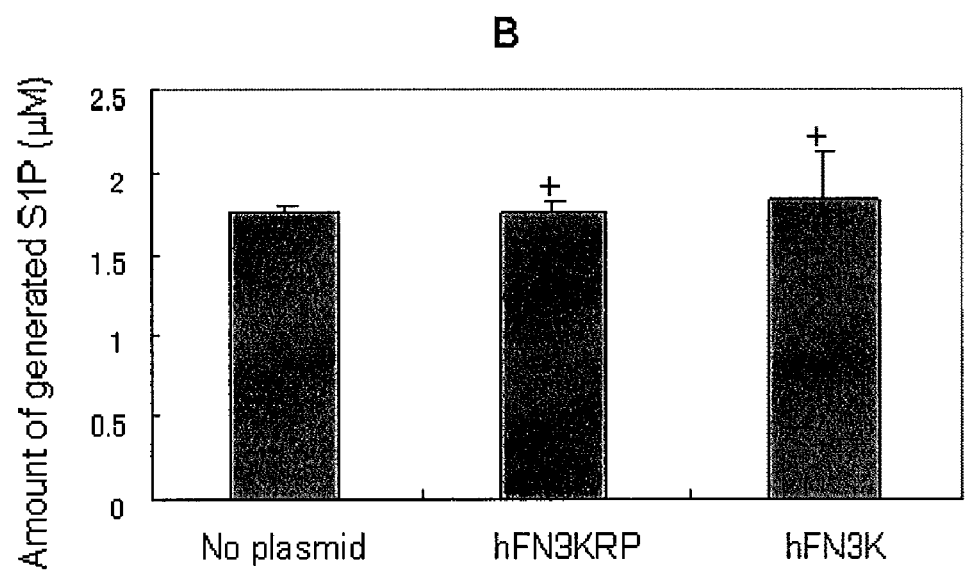

The invention claimed is:

1. A method of determining the ability of a patient to generate the phosphoric ester of the compound represented by general formula (I), which comprises the following steps (1) and (2):

(1) measuring the expression level of a polypeptide in a blood sample collected from a subject, wherein the polypeptide is selected from the group consisting of:

(a) a polypeptide having the amino acid sequence of amino acid residues 1-309 of SEQ ID NO: 2 in the sequence listing; and (b) a polypeptide having the amino acid sequence of amino acid residues 1-309 of SEQ ID NO: 4 in the sequence listing; and (2) comparing the expression level of the polypeptide measured in (1) above with the expression level of said polypeptide in a sample that has been confirmed as having the ability to phosphorylate in vivo the compound represented by general formula (I), so as to examine the ability of the subject to phosphorylate the compound represented by general formula (I), wherein the compound represented by general formula (I) has the formula:

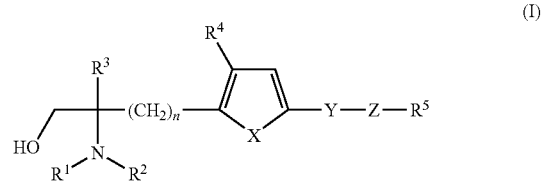

wherein each of $R^1$ and $R^2$ represents a hydrogen atom; $R^3$ represents a C1-C6 alkyl group or a hydroxymethyl group; $R^4$ represents a hydrogen atom, a halogen atom or a C1-C6 alkyl group; $R^5$ represents a phenyl group, a phenyl group which is substituted with 1 to 3 substituents selected from the group consisting of a halogen atom, a cyano group, a C1-C6 alkyl group, a C1-C6 alkoxy group, a C3-C6 cycloalkyl group, a halogeno C1-C6 alkyl group, a phenyl group and a benzyloxy group, a halogen atom or a hydrogen atom; X represents a vinylene group (CH=CH group), an oxygen atom, a sulfur atom or a methylamino group;

Y represents a single bond, an oxygen atom, a sulfur atom or a carbonyl group; Z represents a single bond or a C1-C8 alkylene group; and n is 2 or 3.

2. The method according to claim 1, wherein the sample is peripheral blood.

3. The method according to claim 1, wherein the compound represented by general formula (I) has the formula:
wherein each of $R^1$ and $R^2$ represents a hydrogen atom; $R^3$ represents a methyl group; $R^4$ represents a hydrogen atom; $R^5$ represents a phenyl group which is substituted with 1 to 3 substituents selected from the group consisting of a methyl group; X represents a methylamino group; Y represents a carbonyl group; Z represents trimethylene group or tetramethylene; and n is 2 or 3.

4. The method according to claim 1, wherein the compound represented by general formula (I) is (2R)-2-amino-2-methyl-4{1-methyl-5-[4-(4-methylphenyl)butanoyl]-pyrrol-2-yl}butan-1-ol.

* * * * *